US012789014B2

(12) United States Patent
Liao et al.

(10) Patent No.: US 12,789,014 B2
(45) Date of Patent: Nov. 10, 2026

(54) RADIATION THERAPY SYSTEM

(71) Applicant: SHANGHAI UNITED IMAGING HEALTHCARE CO., LTD., Shanghai (CN)

(72) Inventors: Can Liao, Shanghai (CN); Bo Cai, Shanghai (CN); Ling-Qing Mei, Shanghai (CN); Zhi-Du Zhang, Shanghai (CN); Cheng Ni, Shanghai (CN); Wei Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 376 days.

(21) Appl. No.: 18/369,776

(22) Filed: Sep. 18, 2023

(65) Prior Publication Data

US 2024/0091561 A1 Mar. 21, 2024

(30) Foreign Application Priority Data

Sep. 19, 2022 (CN) ......................... 202211147714.6

(51) Int. Cl.
*A61N 5/10* (2006.01)
*A61B 6/03* (2006.01)
*A61B 6/40* (2024.01)

(52) U.S. Cl.
CPC ............ *A61N 5/1081* (2013.01); *A61B 6/032* (2013.01); *A61B 6/4014* (2013.01)

(58) Field of Classification Search
CPC ................ A61N 5/1081; A61N 5/1049; A61N 2005/1061; A61B 6/032; A61B 6/4014
See application file for complete search history.

(56) References Cited

U.S. PATENT DOCUMENTS

2011/0301449 A1* 12/2011 Maurer, Jr. ............ A61B 6/032 378/65
2015/0131774 A1* 5/2015 Maurer, Jr. .............. A61N 5/10 378/11
2016/0114191 A1* 4/2016 Sankey ................ A61N 5/1049 378/65

FOREIGN PATENT DOCUMENTS

CN 111093764 B 5/2022

* cited by examiner

*Primary Examiner* — Courtney D Thomas

(57) ABSTRACT

A radiation therapy system is disclosed. The radiation therapy system includes a gantry, a first radiation source, and a second radiation source. The gantry is configured to have a cavity extending in a direction along a rotation axis, and the cavity is configured to house a target object. The first radiation source is mounted on the gantry, and configured to emit a treatment beam to a treatment area of the target object. The second radiation source is mounted on the gantry, and configured to emit an imaging beam to an imaging area of the target object. The treatment area partially overlaps the imaging area. A rotation plane of the first radiation source and a rotation plane of the second radiation source are distributed in a direction along the rotation axis.

19 Claims, 18 Drawing Sheets

RADIATION THERAPY SYSTEM

CROSS-REFERENCE TO RELATED APPLICATIONS

The present application claims priority to Chinese patent application No. 202211147714.6, filed on Sep. 19, 2022, the entire contents of which are incorporated herein by reference.

TECHNICAL FIELD

The present disclosure relates to the technical field of medical equipment, and in particular, to a radiation therapy system.

BACKGROUND

Radiation therapy is a localized treatment for a specific target tissue (e.g., a malignant tumor). In order to irradiate a tumor site more accurately and better protect critical organs around the tumor, most of traditional radiation therapy systems integrate a variety of imaging components to perform pre-treatment image guidance, and position monitoring or tracking treatment during treatment on a treatment target area. In the related art, when a treatment component or an imaging component rotates relative to a target object, mutual occlusion between the two components is very likely to occur, thus forming some blind spots that cannot be imaged during a treatment process, thereby affecting the judgment of the entire treatment situation, and even causing misjudgment.

SUMMARY

The present disclosure provides a radiation therapy system, including a gantry having a rotation axis, a first radiation source, and at least one second radiation source. The first radiation source is mounted on the gantry, and configured to emit a treatment beam to a treatment area of a target object. The at least one second radiation source is mounted on the gantry, and configured to emit an imaging beam to an imaging area of the target object. The treatment area partially overlaps the imaging area. The first radiation source and the at least one second radiation source are rotatable around the rotation axis. A rotation plane of the first radiation source and a rotation plane of the at least one second radiation source are distributed in a direction along the rotation axis.

In an embodiment, at least one of the first radiation source and the at least one second radiation source is mounted on the gantry by an adjustable connecting mechanism.

In an embodiment, a central beam axis of the imaging beam and the rotation axis of the gantry form an included angle of $\theta$, the included angle forms a projection angle of $\theta'$ on a horizontal plane, and the $\theta'$ satisfies following conditions: $0° \leq \theta' < 90°$.

In an embodiment, the $\theta$ is 30°, 45° or 60°.

In an embodiment, when a vertical line passing through an isocenter of the radiation therapy system is set as a reference line, the central beam axis of the imaging beam and the reference line form an included angle of $\beta$, the included angle forms a projection angle of $\beta'$ on a vertical plane where the rotation axis of the gantry is positioned, and the $\beta'$ satisfies following conditions: $0° < \beta' \leq 90°$.

In an embodiment, when a vertical line passing through an isocenter of the radiation therapy system is set as a reference line, the central beam axis of the imaging beam and the reference line form an included angle of $\beta$, the included angle forms a projection angle of $\beta''$ on the rotation plane of the first radiation source, and the $\beta''$ satisfies following conditions: $0° \leq \beta'' \leq 90°$.

In an embodiment, the first radiation source and the at least one second radiation source are relatively fixed on the gantry.

In an embodiment, the gantry is configured to drive the first radiation source and the at least one second radiation source such that the first radiation source and the at least one second radiation source rotate synchronously.

In an embodiment, the radiation therapy system further includes a first detector arranged opposite to the first radiation source. The first detector is mounted on the gantry, and the first detector is configured to receive at least part of the treatment beam.

The radiation therapy system further includes a second detector arranged opposite to a corresponding one of the at least one second radiation source. The second detector is mounted on the gantry, and the second detector is configured to receive at least part of the imaging beam.

In an embodiment, a side of the first detector facing the first radiation source is arcuate, and/or a side of the second detector facing the corresponding second radiation source is arcuate.

In an embodiment, the radiation therapy system further includes a third detector configured to receive at least part of the treatment beam and at least part of the imaging beam.

In an embodiment, the number of the at least one second radiation source is two, and the two second radiation sources are spaced apart.

In an embodiment, the radiation therapy system further includes a first imaging component and a second imaging component. The first imaging component includes the at least one second radiation source. The second imaging component is mounted on the gantry. The second imaging component and the first radiation source are arranged in a same radial plane of the gantry.

In an embodiment, the second imaging component includes a third radiation source and a fourth detector arranged opposite to the third radiation source. The third radiation source is configured to emit a further imaging beam to the imaging area of the target object, and the fourth detector is configured to receive at least part of the further imaging beam.

In an embodiment, when the number of the at least one second radiation source is two, the two second radiation sources are arranged on a same side of the third radiation source in the direction along the rotation axis.

In an embodiment, when the number of the at least one second radiation source is two, the two second radiation sources are respectively arranged on different sides of the third radiation source in the direction along the rotation axis.

In an embodiment, the first imaging component is a digital X-ray imaging component, and the second imaging component is an electronic computed tomography imaging component.

DETAILED DESCRIPTION OF THE EMBODIMENTS

Figure 1:
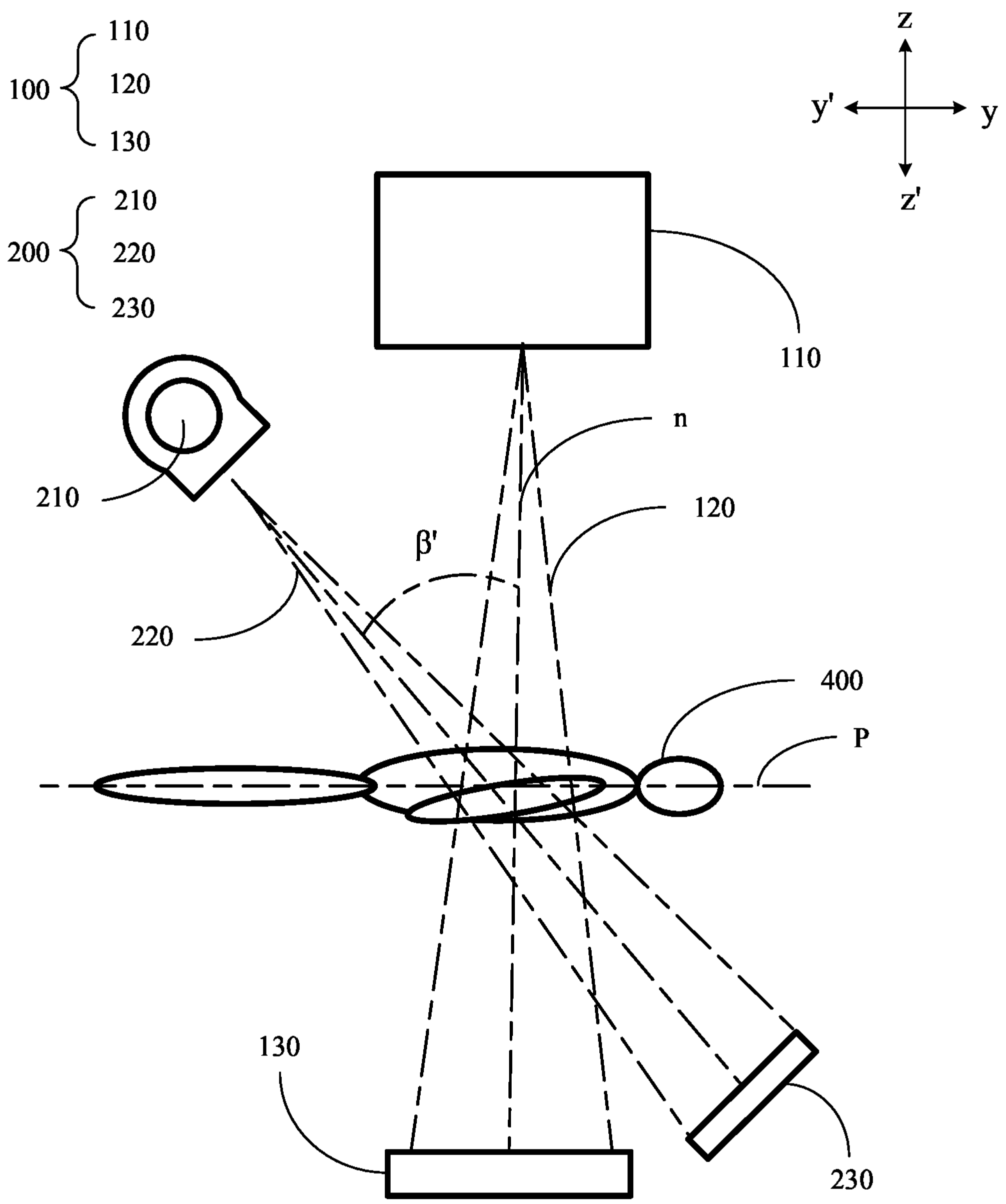
FIG. 1 is a schematic diagram illustrating a radiation therapy system according to a first embodiment of the present disclosure.

In order to make the above objectives, features and advantages of the present disclosure more obvious and understandable, specific implementations of the present disclosure are described in detail below with reference to the accompanying drawings. In the following description, many specific details are set forth in order to fully understand the present disclosure. However, the present disclosure can be implemented in many other ways different from those described herein, and those skilled in the art can make similar improvements without departing from the connotation of the present disclosure. Therefore, the present disclosure is not limited by the specific embodiments disclosed below.

In the description of the present disclosure, it should be understood that the orientation or position relationship indicated by the terms "center", "longitudinal", "transverse", "length", "width", "thickness", "upper", "lower", "front", "back", "left", "right", "vertical", "horizontal", "top", "bottom", "inner", "outer", "clockwise", "counterclockwise", "axial", "radial", "circumferential", etc. are based on the orientation or position relationship shown in the accompanying drawings and are merely intended to facilitate the description of the present disclosure and simplify the description, rather than indicating or implying that the indicated device or element must have a particular orientation or be constructed and operated in a particular orientation, and therefore are not to be interpreted as limiting the present disclosure.

In addition, the terms "first" and "second" are used for descriptive purposes only, and cannot be interpreted as indicating or implying relative importance or implicitly specifying the quantity of indicated technical features. Thus, the features defined as "first" and "second" may explicitly or implicitly include at least one of these features. In the description of the present disclosure, "plurality" means at least two, such as two, three, etc., unless otherwise clearly and specifically defined.

In the present disclosure, unless otherwise clearly specified and limited, the terms "mounted", "connected", "connection", "fixation" and other terms should be understood in a broad sense, for example, it may be a fixed connection or a detachable connection, or integrated; it may be a mechanical connection or an electrical connection; it may be a direct connection or an indirect connection through an intermediate medium, and it may be an internal connection between two elements or an interaction relationship between the two elements, unless otherwise clearly defined. Those of ordinary skill in the art can understand the specific meanings of the above terms in the present disclosure according to specific situations.

In the present disclosure, unless otherwise clearly specified and limited, a first feature being "on" or "under" a second feature may mean that the first and second features are in direct contact, or the first and second features are in indirect contact through an intermediate medium. Moreover, the first feature being "on", "above" and "over" the second feature may mean that the first feature is directly above or obliquely above the second feature, or simply means that the horizontal height of the first feature is greater than the second feature. The first feature being "under", "beneath" and "below" the second feature may mean that the first feature is directly below or obliquely below the second feature, or simply means that the horizontal height of the first feature is less than the second feature.

It should be noted that when an element is referred to as being "fixed on" or "disposed on" another element, it may be directly on the other element or there may be an intervening element. When the element is referred to as being "connected to" another element, it may be directly connected to the other element or intervening elements may also be present. As used herein, the terms "vertical", "horizontal", "upper", "lower", "left", "right" and similar expressions are for the purpose of illustration only and are not meant to be the only embodiments.

Aiming at the problem that in the traditional radiation therapy system, when a treatment component and an imaging component are rotated relative to a target object, mutual occlusion between the two components is very likely to occur, thus forming some blind spots that cannot be imaged, thereby affecting the judgment of the entire treatment situation. The present disclosure provides an improved radiation therapy system. The radiation therapy system includes a gantry, a first radiation source mounted on the gantry, and at least one second radiation source mounted on the gantry.

The first radiation source is configured to emit a treatment beam to a treatment area of a target object. The at least one second radiation source is configured to emit a first imaging beam to an imaging area of the target object. The treatment area partially overlaps the imaging area. The first radiation source and the at least one second radiation source are rotatable around the rotation axis. A rotation plane of the first radiation source and a rotation plane of the at least one second radiation source are distributed in a direction along the rotation axis.

According to the radiation therapy system provided by the present disclosure, since the first radiation source and the second radiation source are relatively fixed on the gantry, and the first radiation source and the second radiation source are arranged in the direction along the rotation axis of the gantry, the first radiation source and the second radiation source are positioned in different radial planes of the gantry. Further, the second radiation source serving as a part of an imaging component has enough physical space to be integrally integrated with the first radiation source serving as a part of a treatment component on the same gantry. Meanwhile, the first radiation source and the second radiation source may be driven by the gantry to rotate synchronously. As a result, when the target object is treated by the radiation therapy system, the gantry can synchronously drive the first radiation source and the second radiation source to rotate synchronously, so that the treatment beam emitted by the first radiation source is not be blocked by the second radiation source, and the first imaging beam emitted by the second radiation source is not be blocked by the first radiation source. As a result, no blind spot which cannot be imaged will be generated, and an imaging effect in the whole treatment process is better. Furthermore, the judgment of the user on a treatment situation is more accurate, and the misjudgment is not easy to occur.

Figure 3:
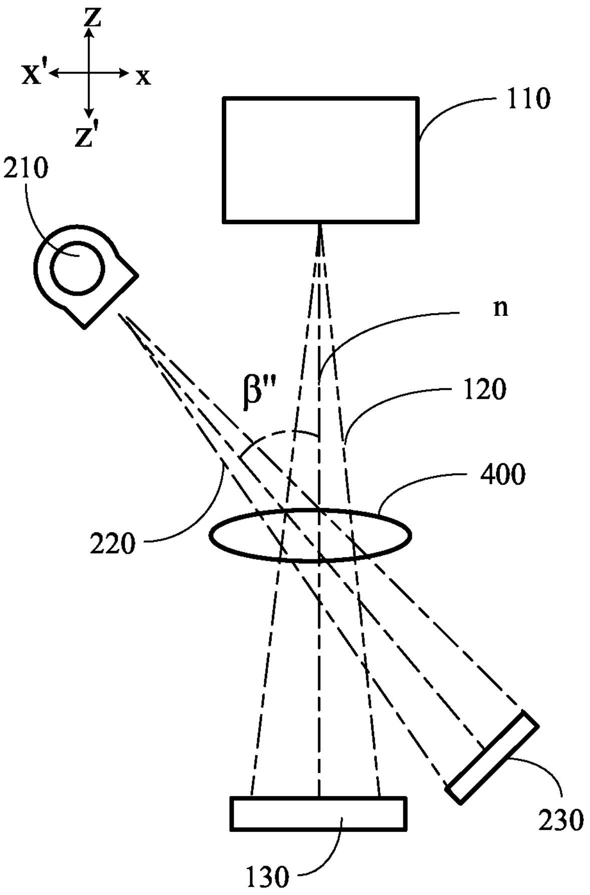
FIG. 3 is a schematic diagram illustrating a radiation therapy system according to a second embodiment of the present disclosure.
Figure 4:
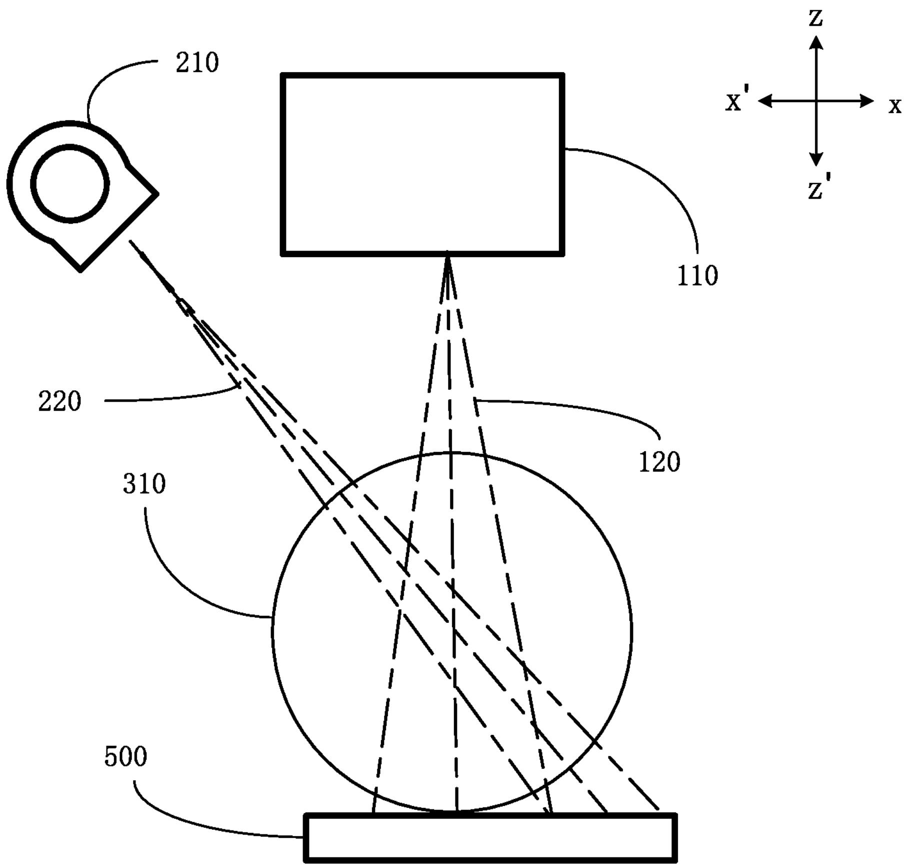
FIG. 4 is a schematic diagram illustrating a radiation therapy system according to a third embodiment of the present disclosure.
Figure 5:
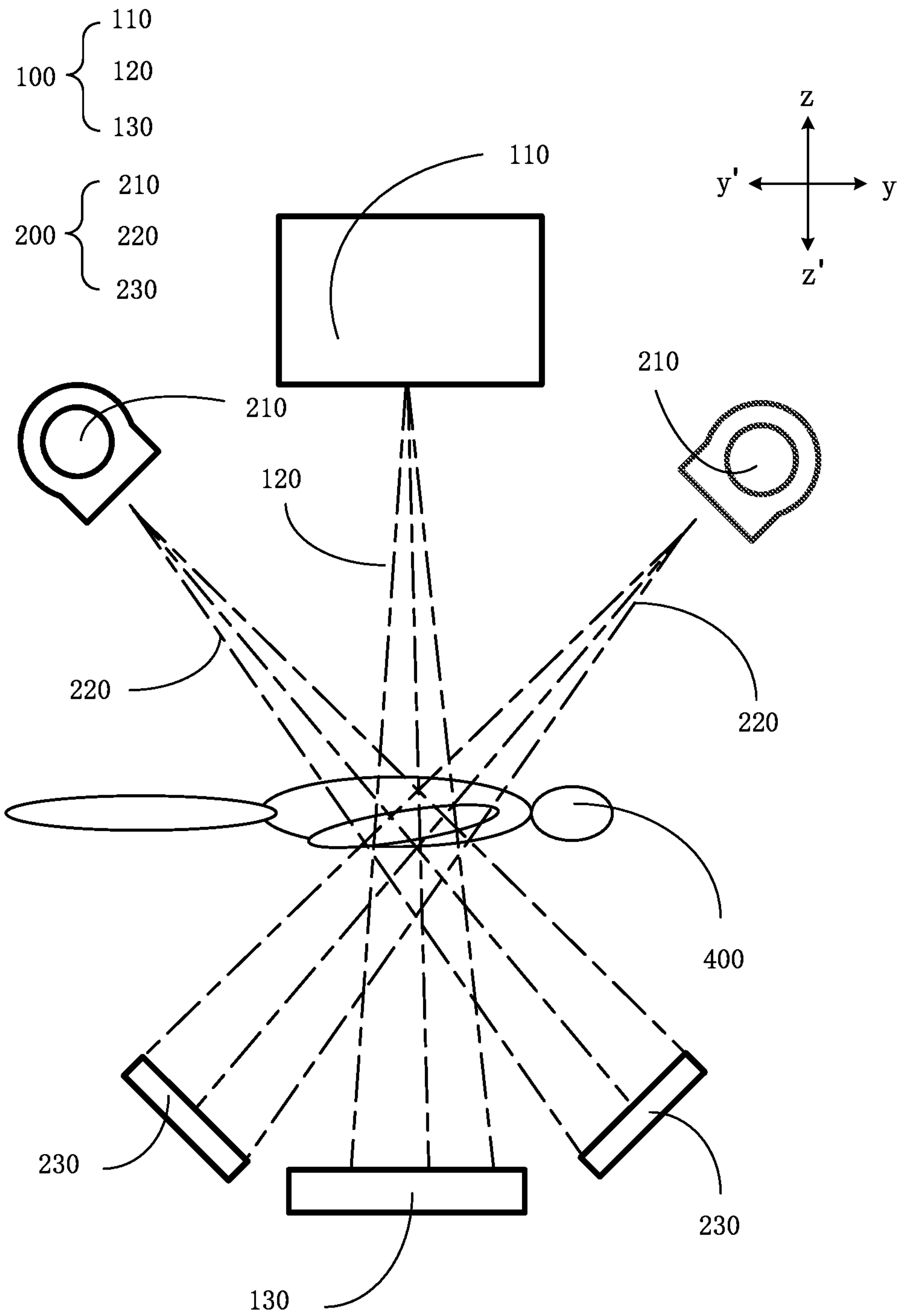
FIG. 5 is a schematic diagram illustrating a radiation therapy system according to a fourth embodiment of the present disclosure.
Figure 10:
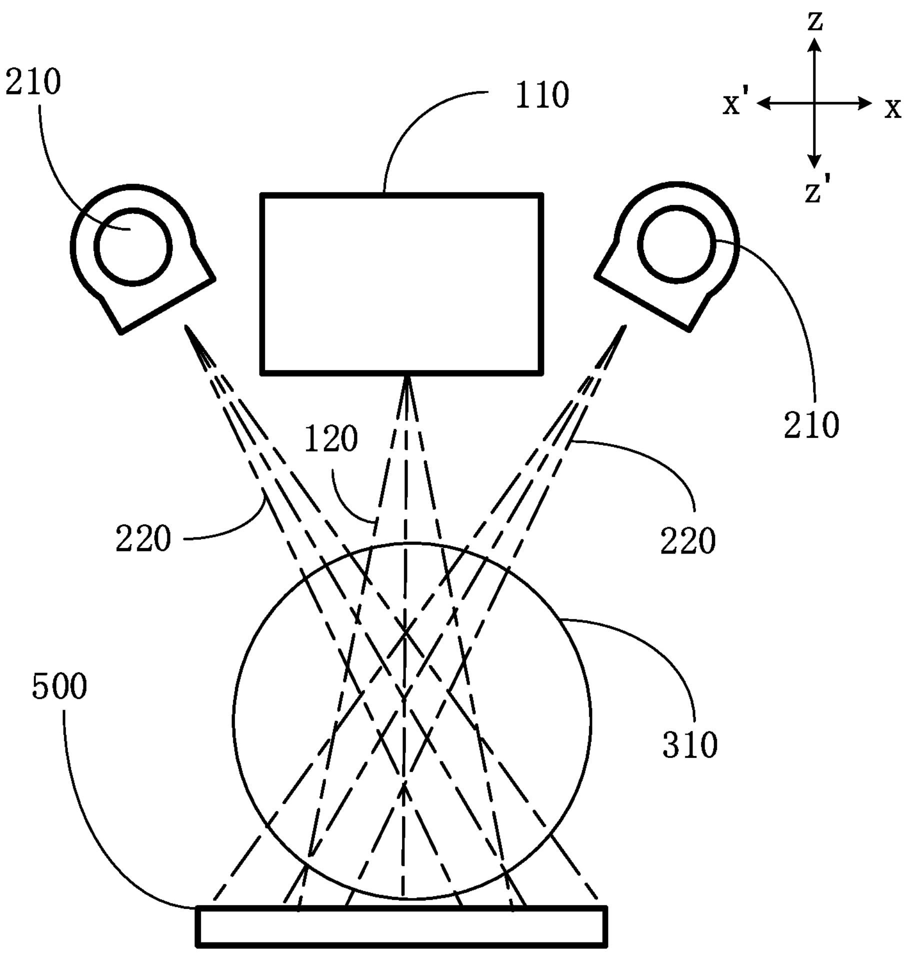
FIG. 10 is a schematic diagram illustrating a radiation therapy system according to an eighth embodiment of the present disclosure.
Figure 11:
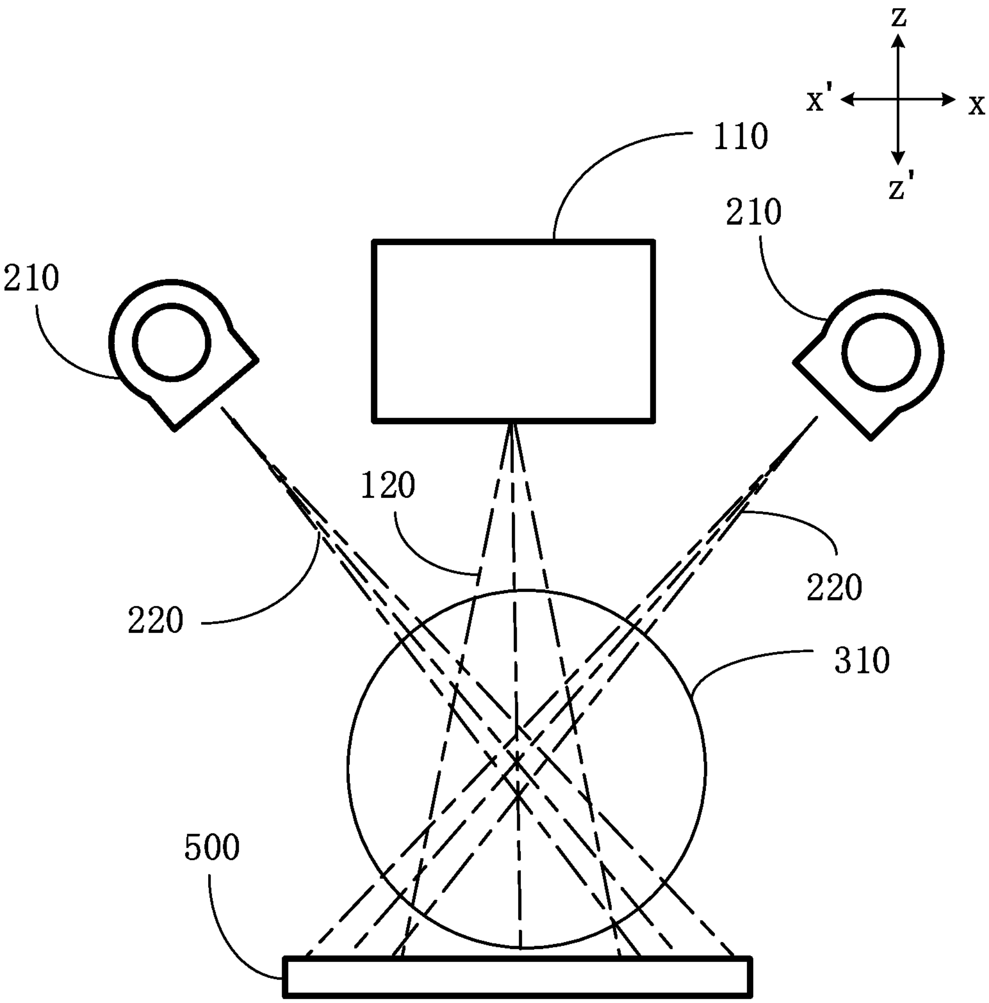
FIG. 11 is a schematic diagram illustrating a radiation therapy system according to a ninth embodiment of the present disclosure.
Figure 12:
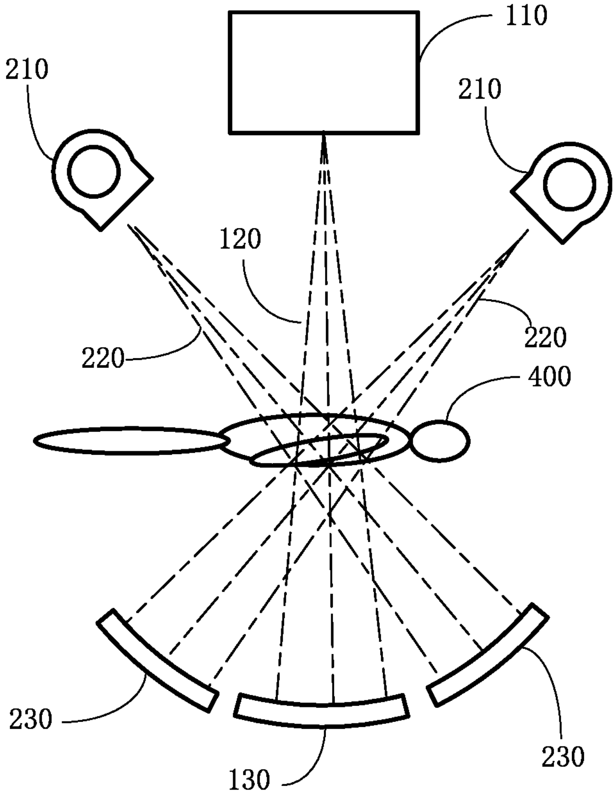
FIG. 12 is a schematic diagram illustrating a radiation therapy system according to a tenth embodiment of the present disclosure.
Figure 13:
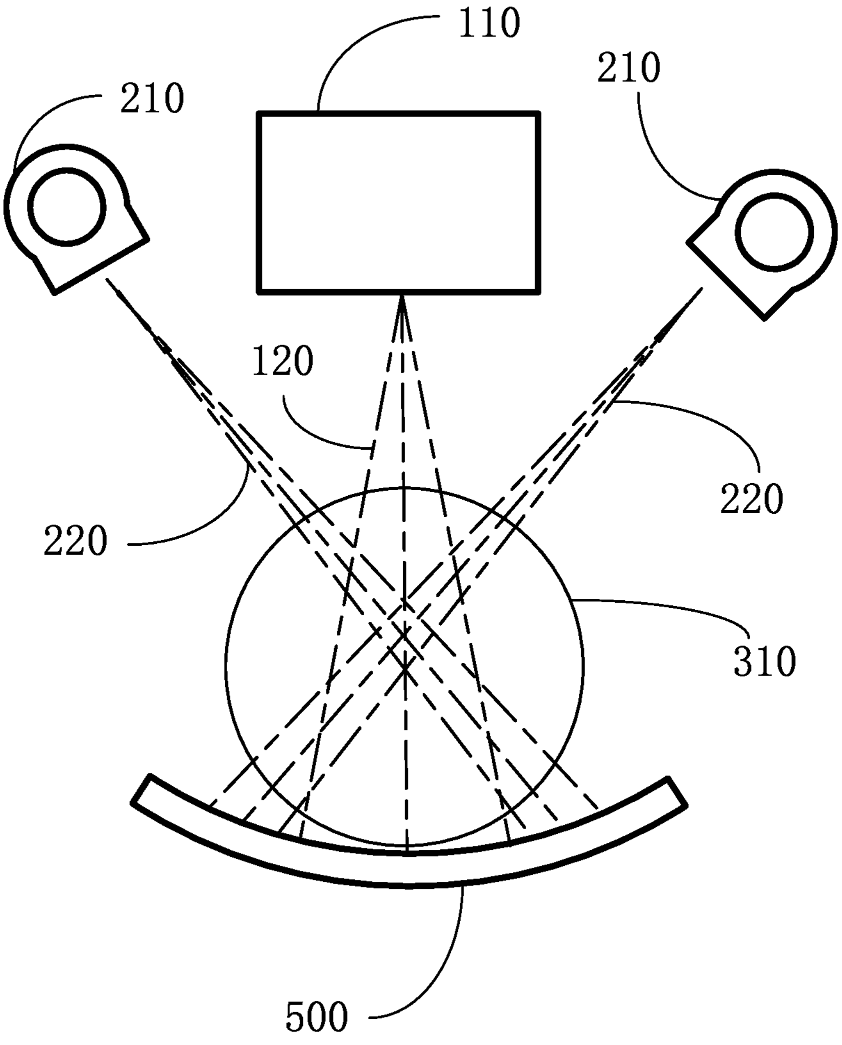
FIG. 13 is a schematic diagram illustrating a radiation therapy system according to an eleventh embodiment of the present disclosure.
Figure 14:
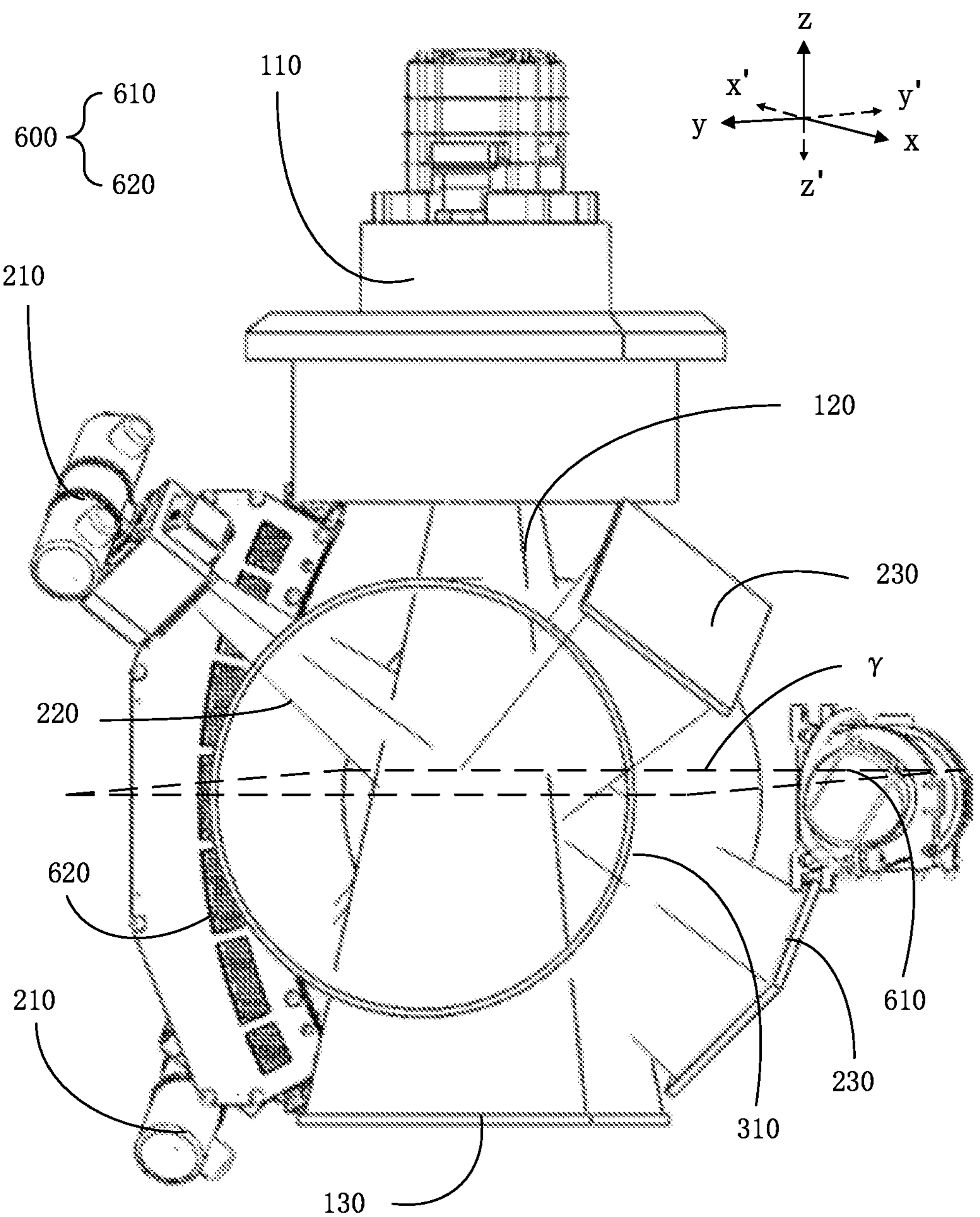
FIG. 14 is a schematic diagram illustrating a radiation therapy system according to a twelfth embodiment of the present disclosure.
Figure 15:
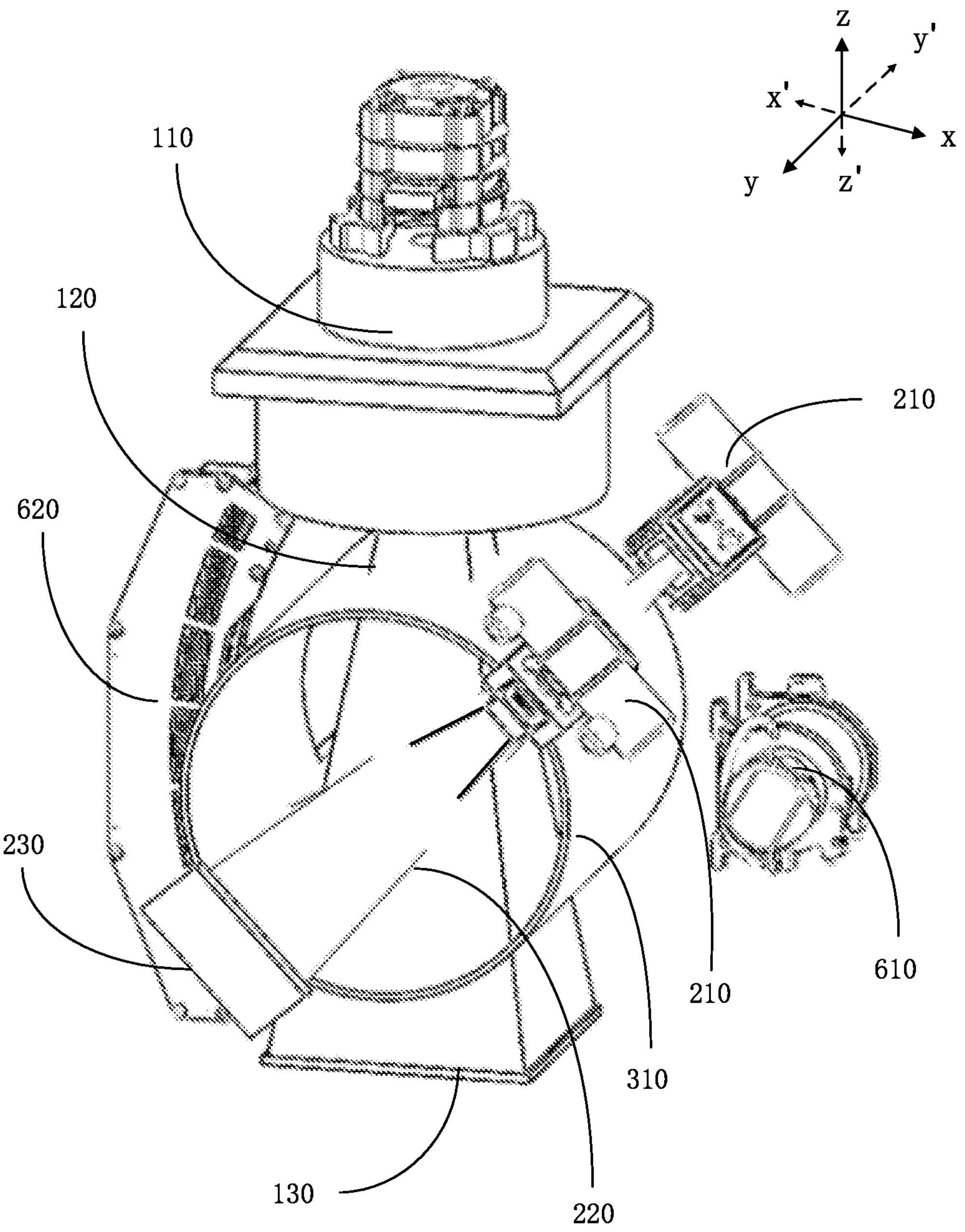
FIG. 15 is a schematic diagram illustrating a radiation therapy system according to a thirteenth embodiment of the present disclosure.
Figure 16:
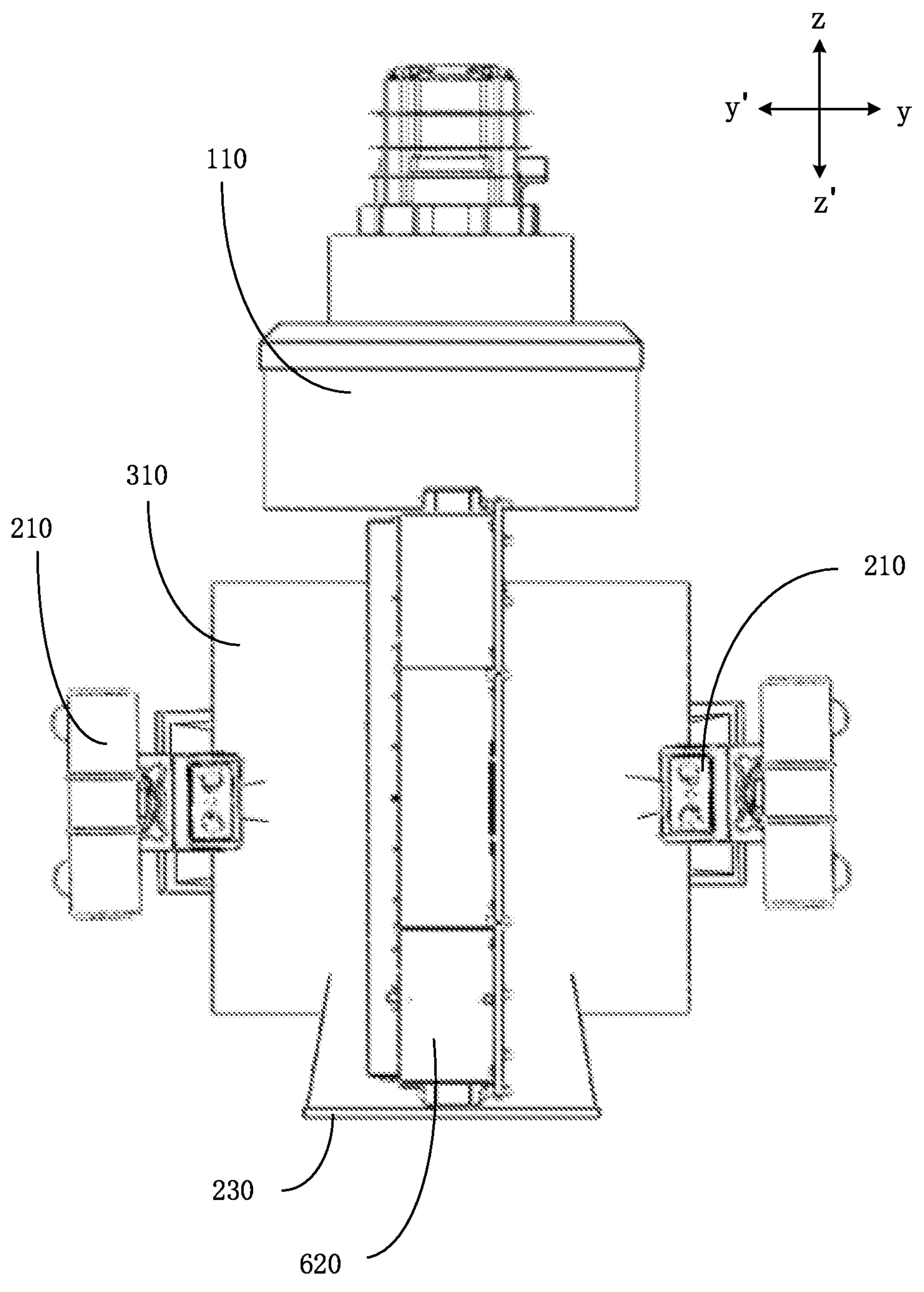
FIG. 16 is a schematic diagram illustrating a radiation therapy system according to a fourteenth embodiment of the present disclosure.
Figure 17:
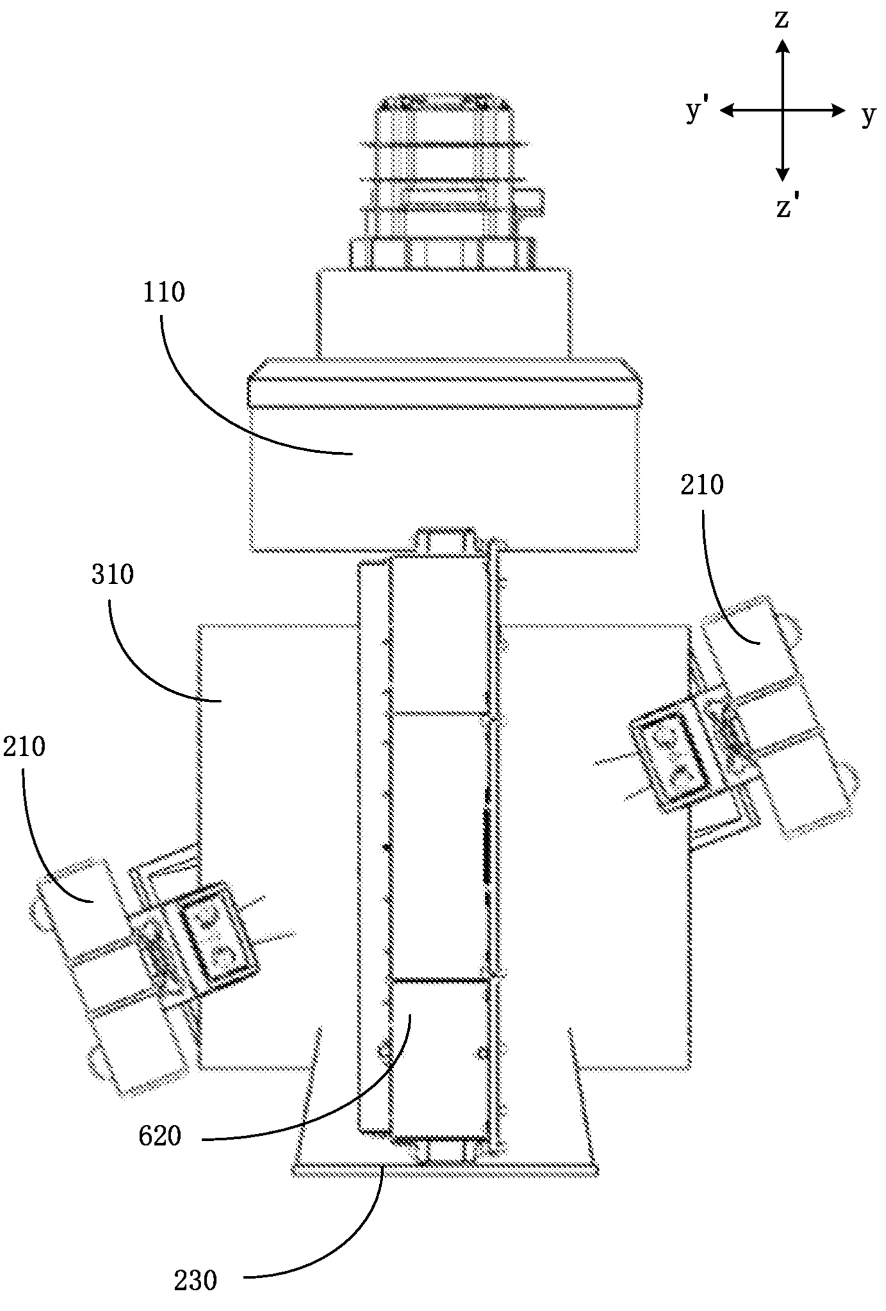
FIG. 17 is a schematic diagram illustrating a radiation therapy system according to a fifteenth embodiment of the present disclosure.

Referring FIGS. 1, 3 to 5, and 10 to 17, FIG. 1 is a schematic diagram illustrating a radiation therapy system according to a first embodiment of the present disclosure, FIG. 3 is a schematic diagram illustrating a radiation therapy system according to a second embodiment of the present disclosure, FIG. 4 is a schematic diagram illustrating a radiation therapy system according to a third embodiment of the present disclosure, FIG. 5 is a schematic diagram illustrating a radiation therapy system according to a fourth embodiment of the present disclosure, FIG. 10 is a schematic diagram illustrating a radiation therapy system according to an eighth embodiment of the present disclosure, FIG. 11 is a schematic diagram illustrating a radiation therapy system according to a ninth embodiment of the present disclosure, FIG. 12 is a schematic diagram illustrating a radiation therapy system according to a tenth embodiment of the present disclosure, FIG. 13 is a schematic diagram illustrating a radiation therapy system according to an eleventh embodiment of the present disclosure, FIG. 14 is a schematic diagram illustrating a radiation therapy system according to a twelfth embodiment of the present disclosure, FIG. is a schematic diagram illustrating a radiation therapy system according to a thirteenth embodiment of the present disclosure, FIG. 16 is a schematic diagram illustrating a radiation therapy system according to a fourteenth embodiment of the present disclosure, and FIG. 17 is a schematic diagram illustrating a radiation therapy system according to a fifteenth embodiment of the present disclosure.

A radiation therapy system is provided by an embodiment of the present disclosure. The radiation therapy system includes a gantry 300, a first radiation source 110 and a second radiation source 210. The gantry 300 is rotatable and has a rotation axis p. The first radiation source 110 is mounted on the gantry 300, and the first radiation source 110 is configured to emit a treatment beam 120 to a treatment area of a target object 400. The second radiation source 210 is mounted on the gantry 300, and the second radiation source 210 is configured to emit a first imaging beam 220 to an imaging area of the target object 400. The treatment area partially overlaps the imaging area. The first radiation source 110 and the second radiation source 210 are drivable by the gantry 300 to rotate around the rotation axis p of the gantry 300 synchronously. A rotation plane of the first radiation source 110 and a rotation plane of the second radiation source 210 are distributed in a direction along the rotation axis p.

In the radiation therapy system provided by the present disclosure, since the first radiation source 110 and the second radiation source 210 are relatively fixed on the gantry 300, and the rotation plane of the first radiation source 110 and the rotation plane of the second radiation source 210 are arranged in the direction along the rotation axis of the gantry 300, the first radiation source 110 and the second radiation source 210 are positioned in different radial planes of the gantry 300, such as shown in FIG. 16 and FIG. 17. Further, the second radiation source 210 serving as a part of a first imaging component 200 has enough physical space to be integrally integrated with the first radiation source 110 serving as a part a treatment component 100 on the same gantry 300. Meanwhile, when the target object 400 is treated by the radiation therapy system, the gantry 300 can synchronously drive the first radiation source 110 and the second radiation source 210 to rotate synchronously, so that the treatment beam 120 emitted by the first radiation source 110 is not be blocked by the second radiation source 210, and the first imaging beam 220 emitted by the second radiation source 210 is not be blocked by the first radiation source 110. As a result, no blind spot which cannot be imaged will be generated, and the imaging effect in the whole treatment process is better. Furthermore, the judgment of the user on the treatment situation is more accurate, and the misjudgment is not easy to occur.

It should be noted that the radial planes at different positions in the rotation axis of the gantry are different radial planes of the gantry. For example, when the first radiation source 110 and the second radiation source 210 are spaced apart in an axial direction of the gantry, their rotation planes are different, and thus they are positioned in the different radial planes of the gantry.

In an embodiment, the target object 400 is a treatment couch. In another embodiment, the target object 400 is a treatment object. In some other embodiments, the target object 400 is a phantom used before treatment.

It should be noted that, each of the first radiation source 110 and the second radiation source 210 can emit one or more radiations, such as X-rays, α-rays, β-rays, γ-rays, electron beams, proton beams and the like.

Referring FIGS. 2A, 4, 10, 11 and 13 to 17, in some embodiments, the gantry 300 of the radiation therapy system is configured to have a cavity 310 extending in the direction along its own rotation axis p, and the cavity 310 is configured to house the target object 400. Specifically, the cavity 310 of the gantry may be circular, polygonal or any other irregular shape, which is not particularly limited thereto.

It should be noted that, in some embodiments, the treatment area is positioned at a center of the cavity 310. In some other embodiments, the treatment area is positioned at any position inside the cavity 310, and the imaging area is set accordingly. Specifically, the imaging area and the treatment area overlap completely or partially.

In some embodiments, the radiation therapy system further includes an additional gantry, which is fixed relative to the ground. The gantry is mounted on the additional gantry and can rotate relative to the additional gantry, so as to drive the first radiation source 110 and the second radiation source 210 to rotate relative to the target object 400.

Specifically, the radiation therapy system includes the treatment component 100. The treatment component 100 includes the first radiation source 110 and other first components. The other first components may be mounted on the gantry, or mounted on other system components such as the additional gantry, or fixedly mounted on the ground, which is not particularly limited thereto.

The radiation therapy system further includes the first imaging component 200. The first imaging component 200 includes the second radiation source 210 and other second components. The other second components can be mounted on the gantry, or mounted on other system components such as the additional gantry, or fixedly mounted on the ground, which is not particularly limited thereto.

It should be noted that when the radiation therapy system performs imaging during the treatment process, some scattered rays generated by the treatment beam 120 may interfere with the imaging. In order to avoid mutual interference between the treatment beam 120 and the first imaging beam 220, imaging may be performed in the gap between emissions of the treatment beam 120, such that the treatment beam 120 and the first imaging beam 220 do not operate simultaneously.

Specifically, the treatment beam 120 is generally a pulse beam, with a typical pulse period of 5 ms, a pulse width of 5 μs, and a duty ratio of 1/1000. That is, in each pulse period, the first radiation source 110 emits the treatment beam 120 for 5 μs, and the second radiation source 210 may be controlled to emit the first imaging beam 220 within the gap of 4.995 ms between the emissions of the treatment beam. In this way, by controlling the emitting time of the treatment beam 120 and the first imaging beam 220, the first imaging beam 220 is emitted between the pulse intervals of the treatment beam 120.

For a static plan, when a mechanical component such as a tungsten jaw, a multi-leaves collimator (MLC), or a gantry moves, the emission of the treatment beam 120 will be stopped, and the first imaging beam 220 may be controlled to emit to perform imaging during this process.

For a dynamic plan, when the mechanical component such as the tungsten jaw, the multi-leaves collimator (MLC), or the gantry moves, the emission of the treatment beam 120 is maintained. A time point when the imaging is performed can be set when making a radiotherapy plan. At this time point, a dose rate of the treatment beam 120 is set to zero, and the first imaging beam 220 is controlled to emit to perform imaging.

Figure 6:
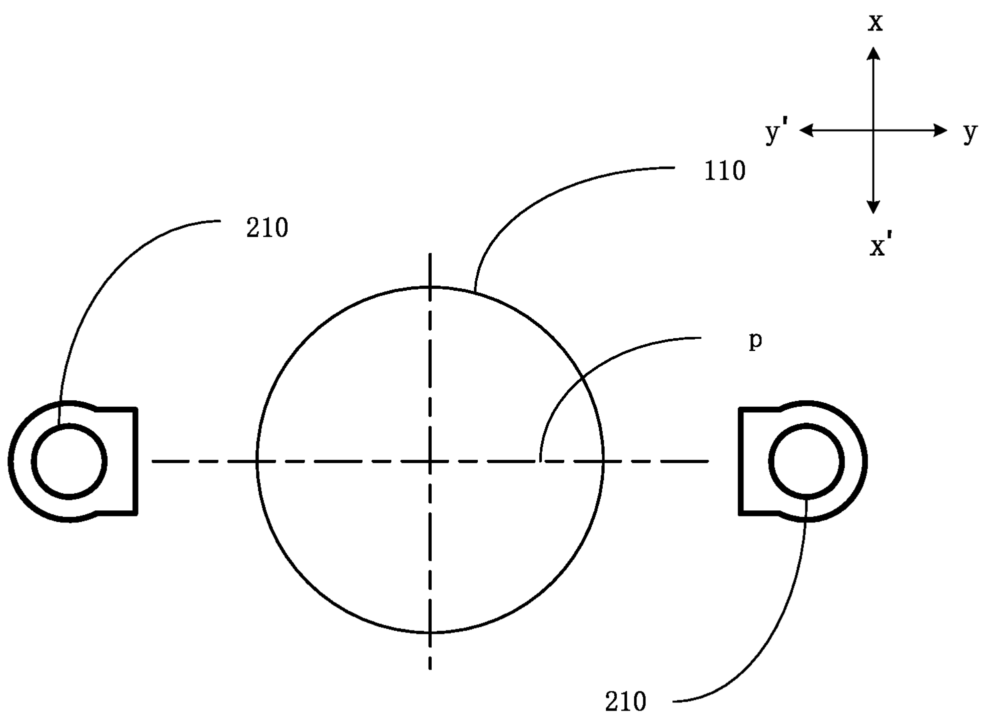
FIG. 6 is a top view of the radiation therapy system illustrated in FIG. 5.
Figure 7:
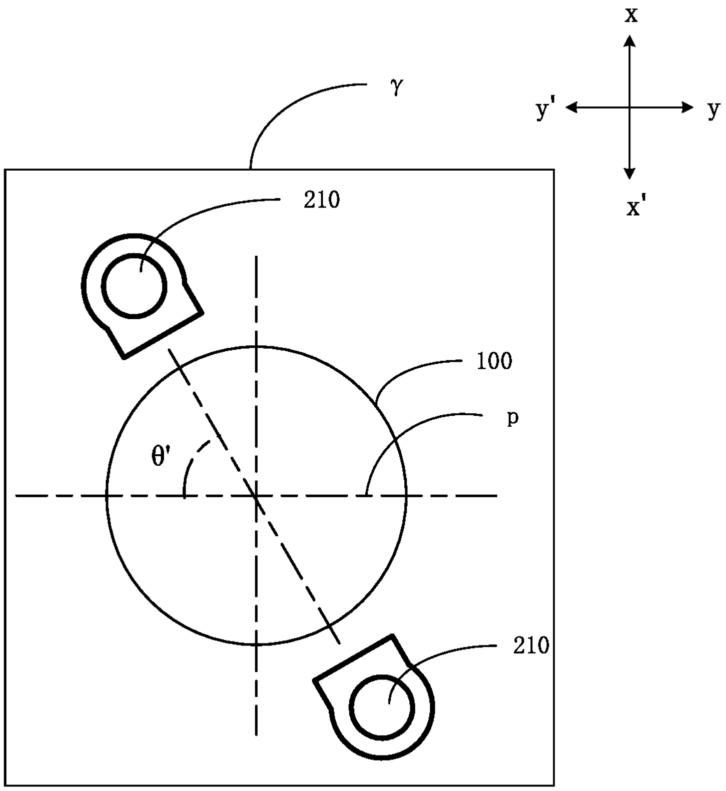
FIG. 7 is a schematic diagram illustrating a radiation therapy system according to a fifth embodiment of the present disclosure.
Figure 8:
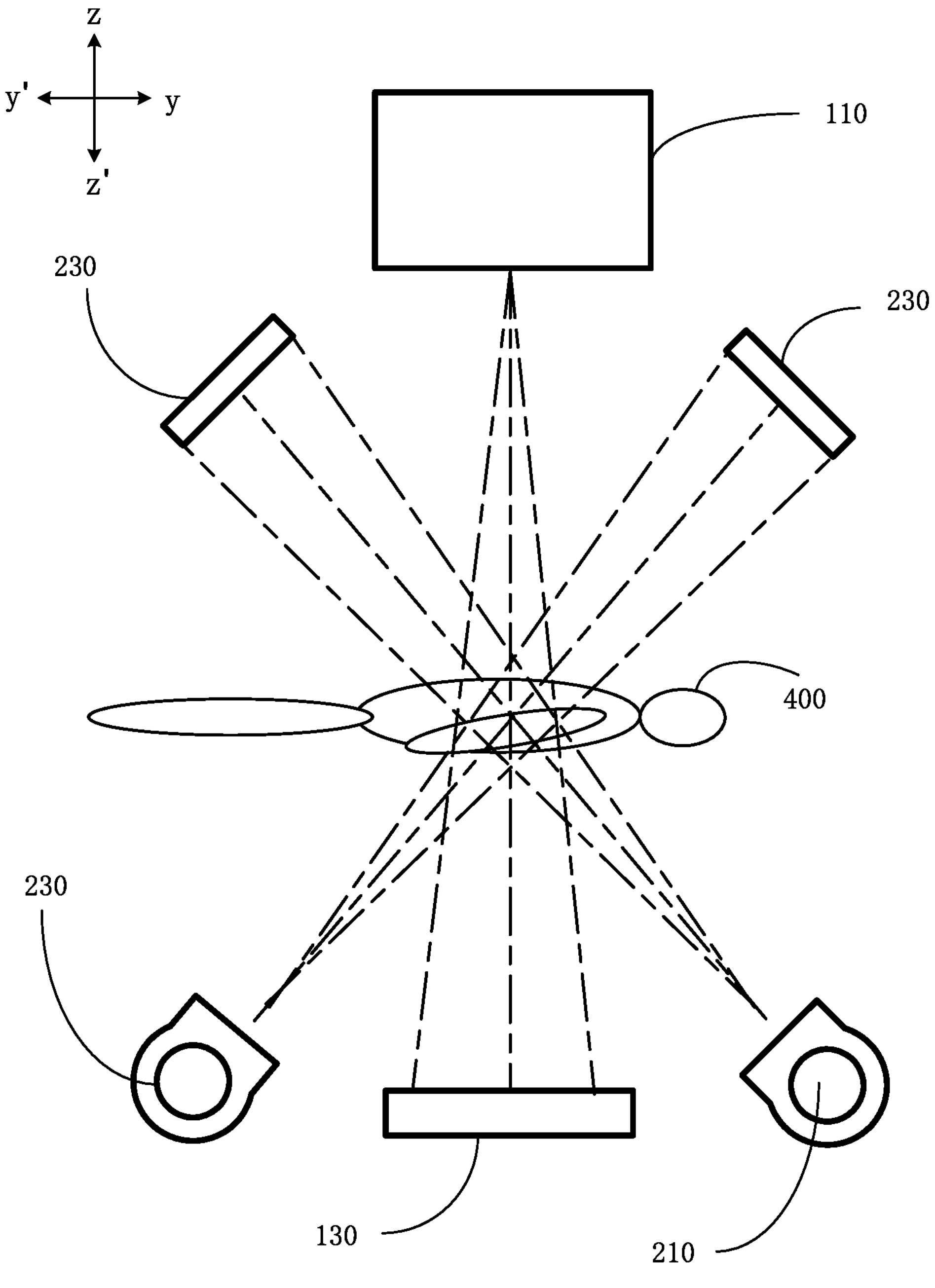
FIG. 8 is a schematic diagram illustrating a radiation therapy system according to a sixth embodiment of the present disclosure.
Figure 9:
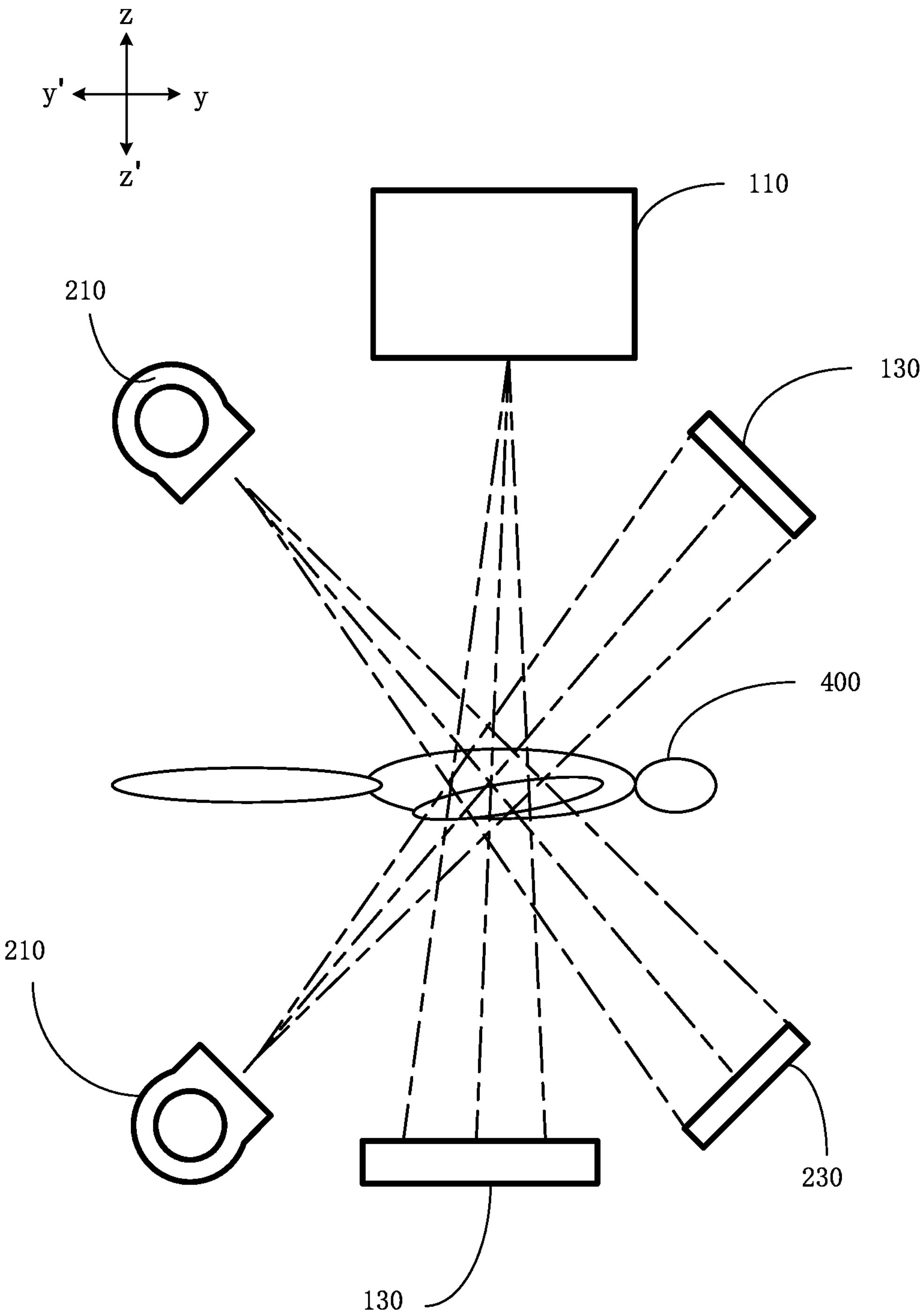
FIG. 9 is a schematic diagram illustrating a radiation therapy system according to a seventh embodiment of the present disclosure.

The configuration of the radiation therapy system will be specifically described below. Referring to FIGS. 2 to 9, FIG. 2 shows a top view of the radiation therapy system illustrated in FIG. 1, FIG. 6 shows a top view of the radiation therapy system illustrated in FIG. 5, FIG. 7 is a schematic diagram illustrating a radiation therapy system according to a fifth embodiment of the present disclosure, FIG. 8 is a schematic diagram illustrating a radiation therapy system according to a sixth embodiment of the present disclosure, and FIG. 9 is a schematic diagram illustrating a radiation therapy system according to a seventh embodiment of the present disclosure.

Figure 2:
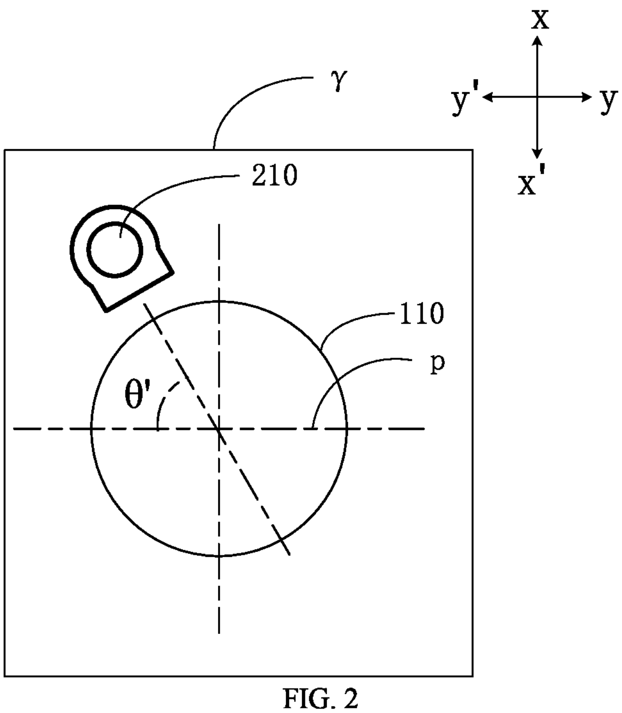
FIG. 2 is a top view of the radiation therapy system illustrated in FIG. 1.
Figure 2A:
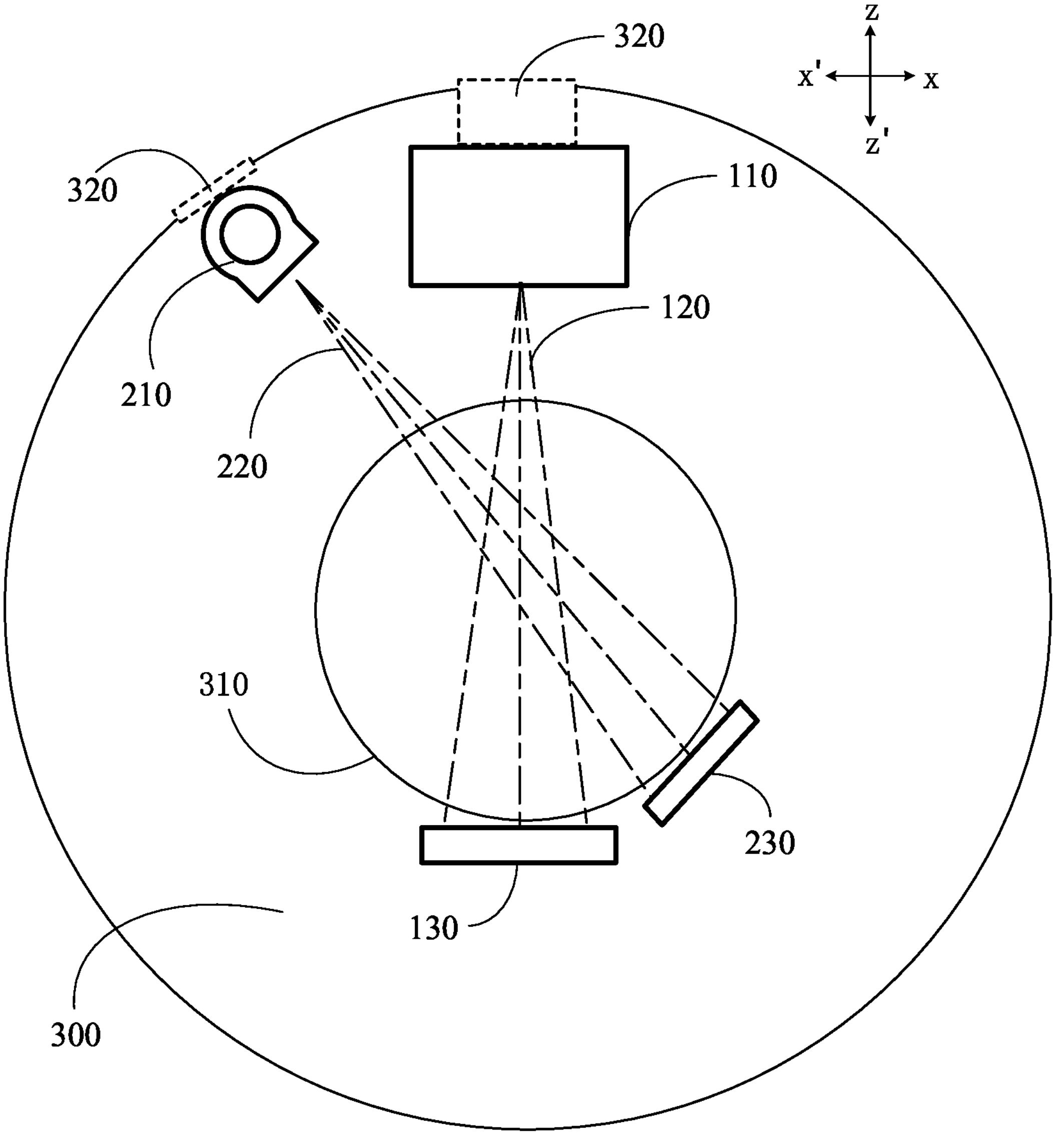
FIG. 2A is a schematic diagram illustrating an axial cross section of the radiation therapy system illustrated in FIG. 1.

Referring to FIG. 2A, at least one of the first radiation source 110 and the second radiation source 210 of the radiation therapy system according to some embodiments of the present disclosure is mounted on the gantry 300 by an adjustable connecting mechanism 320, a line connecting the first radiation source 110 and an isocenter of the radiation therapy system and a line connecting the second radiation source 210 and the isocenter of the radiation therapy system forms a preset included angle. Since at least one of the first radiation source 110 and the second radiation source 210 is mounted on the gantry 300 by the adjustable connecting mechanism 320, the mounting position of the first radiation source 110 or the second radiation source 210 relative to the gantry 300 can be changed by the adjustable connecting mechanism 320, so that the position of the first radiation source 110 relative to the second radiation source 210 is changed, and the magnitude of the preset included angle between the line connecting the first radiation source 110 and the isocenter of the radiation therapy system and the line connecting the second radiation source 210 and the isocenter of the radiation therapy system can be changed to adapt to different mounting requirements. Specifically, when it is necessary to further mount a computed tomography (CT) imaging component (such as an electronic computed tomography imaging component) on the radiation therapy system, the mounting position of the first radiation source 110 or the second radiation source 210 relative to the gantry 300 can be changed by the adjustable connecting mechanism 320, so that the CT imaging component and the treatment component 100 are mounted in the same radial plane of the gantry 300.

In an embodiment, the first radiation source 110 is mounted on the gantry 300 by the adjustable connecting mechanism 320, and the positional relationship between the two radiation sources can be changed by adjusting the mounting position of the first radiation source 110 relative to the gantry 300.

In another embodiment, the second radiation source 210 is mounted on the gantry 300 by the adjustable connecting mechanism 320, and the positional relationship between the two radiation sources can be changed by adjusting the mounting position of the second radiation source 210 relative to the gantry 300.

In yet another embodiment, as shown in FIG. 2A, the first radiation source 110 and the second radiation source 210 are respectively mounted on the gantry 300 by the adjustable connecting mechanism 320, and the positional relationship between the two radiation sources can be changed by adjusting the mounting position of any one of the first radiation source 110 and the second radiation source 210 relative to the gantry 300.

Specifically, the adjustable connecting mechanism 320 is mounted on the gantry 300, which is a multi-dimensional adjustment mechanism. The adjustable connecting mechanism may extend and move in at least one of the axial direction, a circumferential direction or a radial direction of the gantry, so that the position relationship between the first radiation source 110 and the second radiation source 210 can be adjusted in any of a x-x' direction, a y-y' direction or a z-z' direction in FIG. 14. In other embodiments, the adjustment dimensions and adjustment methods of the multi-dimensional adjustment mechanism can be set according to application requirements.

In some embodiments, the adjustable connecting mechanism includes threaded holes and threaded connectors at different positions on the gantry. The first radiation source 110 or the second radiation source 210 is mounted on the threaded holes at different positions on the gantry by the threaded connectors, thereby realizing the change of the mounting position of the first radiation source 110 or the second radiation source 210 relative to the gantry.

In some other embodiments, the adjustable connecting mechanism includes a first member and a second member that cooperate with each other. The first member is fixedly connected to the gantry, or the first member is realized by the gantry itself. The second member may move relative to the first member, and the first radiation source 110 and/or the second radiation source 120 are arranged on the second member. The mounting positions of the first radiation source 110 and/or the second radiation source 120 can be changed by moving the second member. For example, the adjustable connecting mechanism includes a sliding rail, a sliding block and a locking member that cooperate with each other. The sliding rail is arranged on the gantry, and the sliding block cooperating with the sliding rail is mounted on the sliding rail. The first radiation source 110 or the second radiation source 210 is mounted on the sliding block. When the first radiation source 110 or the second radiation source 210 slides to a preset position relative to the sliding rail by the sliding block, the locking member can lock the sliding block to restrict the sliding block from continuing to slide in an extending direction of the sliding rail, thereby realizing the change of the mounting position of the first radiation source 110 or the second radiation source 210 relative to the gantry.

Referring to FIG. 2, FIG. 6 and FIG. 7, in the radiation therapy system according to some embodiments of the present disclosure, a central beam axis of the first imaging beam 220 and a central beam axis of the treatment beam 120 intersect at the isocenter of the radiation therapy system, and an included angle between the central beam axis of the first imaging beam 220 and the central beam axis of the treatment beam 120 is adjustable.

Specifically, the isocenter of the radiation therapy system according to the embodiments of the present disclosure is the point where the rotation axes of the gantry, the first radiation source 110 and the treatment couch in the cavity 310 intersect, with a center error of ±2 mm.

By adjusting the included angle between the central beam axis of the first imaging beam 220 and the central beam axis of the treatment beam 120, the position of the second radiation source 210 relative to the first radiation source 110 can be changed, thereby adapting to different mounting requirements. For example, when it is necessary to further mount the CT imaging component (such as the electronic computed tomography imaging component) on the radiation therapy system, since the entire CT imaging component has many components and large sizes, a large mounting space is required, and the CT imaging component must be strictly mounted on a same radial plane as the treatment component 100 on the gantry. In this case, the included angle between the central beamline of the first imaging beam 220 and the central beamline of the treatment beam 220 can be adjusted to realize the mounting of the CT imaging component.

Referring to FIG. 2 and FIG. 7, in some embodiments, an included angle between the central beam axis of the first imaging beam 220 and the rotation axis p of the gantry is θ, and a projection angle of θ on a horizontal plane γ is θ' which satisfies following conditions: 0°≤θ'<90°. By changing the included angle between the central beam axis of the first imaging beam 220 and the rotation axis p of the gantry, the position of the second radiation source 210 relative to the first radiation source 110 can be changed, thereby adapting to different mounting requirements.

In an embodiment, when it is necessary to further mount the CT imaging component (such as the electronic computed tomography imaging component) on the radiation therapy system, since the entire CT imaging component has many components and large sizes, the large mounting space is required. The CT imaging component must be strictly mounted on the same radial plane as the treatment component 100 on the gantry. In this case, the included angle θ between the central beam axis of the first imaging beam 220 and the rotation axis p of the gantry is set to a small value, so that when the radiation therapy system is in an initial state, i.e., when the treatment beam 120 is emitted from top to bottom in a vertical direction, the projection angle θ' of θ on the horizontal plane γ is 5° or 10°, etc. As a result, a distance between the second radiation source 210 and the first radiation source 110 in the direction along the rotation axis p of the gantry is relatively long, thereby effectively ensuring the mounting space of the entire CT component. Specifically, because the CT imaging component includes a high-voltage generator, a radiation source, an arcuate detector, and a heat dissipation device, etc., a relatively large mounting space is required.

In still some embodiments, water-cooling components of the radiation therapy system are also mounted on the gantry. In order to avoid these mounting components, the included angle θ between the central beam axis of the first imaging beam 220 and the rotation axis p of the gantry is set to a relatively small value, so that when the radiation therapy system is in the initial state, i.e., when the treatment beam 120 is emitted from top to bottom in the vertical direction, the projected angle θ' of θ on the horizontal plane γ is a small value. As a result, an axial dimension of the entire radiation therapy system in the rotation axis p is relatively large, so that different components can be mounted on the gantry.

In another embodiment, when the radiation therapy system does not need to mount the CT imaging component, the included angle θ between the central beam axis of the first imaging beam 220 and the rotation axis p of the gantry can be set to a larger value, so that when the radiation therapy system is in the initial state, i.e., when the treatment beam 120 is emitted from top to bottom in the vertical direction, the projection angle θ' of θ on the horizontal plane γ is 75° or 85°, etc. As a result, the size of the entire radiation therapy system in an extending direction of the rotation axis p is relatively small and the structure is relatively compact. Specifically, when the second radiation source 210 is rotated around the axis in the z-z' direction in FIG. 14 or FIG. 15, the relative position between the second radiation source 210 and the first radiation source 110 can be changed, so that the included angle θ between the central beam axis of the first imaging beam 220 and the rotation axis p of the gantry changes.

Since the included angle θ' is adjustable to be within the range of 0°-90°, different angles of the included angle θ' can be adaptively selected when the CT imaging component is mounted on the radiation therapy system, so as to adapt to CT imaging components of different sizes and mounting requirements, making the whole radiation therapy system more adaptable. Specifically, when the radiation therapy system is in the initial state, i.e., when the treatment beam 120 is emitted from top to bottom in the vertical direction, and the included angle θ' gradually increases between 0°-90°, the size of the entire radiation therapy system in the direction along the rotation axis p can be reduced, making the entire system more compact.

It should be noted that a specific value of the included angle θ can be selected during a manufacturing process of the radiation therapy system, and when the manufacturing process is completed, the included angle θ will no longer change. It is also possible to configure a plurality of different mounting positions on the gantry, so that the second radiation source 210 is mounted at different mounting positions, thereby changing the magnitude of the included angle θ, which is not limited thereto.

In an embodiment, the included angle θ is 30°. When the included angle θ is 30°, a distance between the second radiation source 210 and the first radiation source 110 in the direction along the rotation axis p is relatively long, so that the CT imaging component is easy to mount.

In another embodiment, the included angle θ is 45°. When the included angle θ is 45°, the distance between the second radiation source 210 and the first radiation source 110 in the direction along the rotation axis p is relatively moderate, so that the CT imaging component is easy to mount, and the size of the entire radiation therapy system in the extending direction of the rotation axis p is also relatively appropriate.

In yet another embodiment, the included angle θ is 60°. When the included angle θ is 60°, the distance between the second radiation source 210 and the first radiation source 110 in the direction along the rotation axis p is relatively short, so that the size of the entire radiation therapy system in the extending direction of the rotation axis p is relatively small and the structure is more compact.

Referring to FIG. 1, in the radiation therapy system according to some embodiments of the present disclosure, a vertical line passing through the isocenter of the radiation therapy system is taken as a reference line n. An included angle between the central beam axis of the first imaging beam 220 and the reference line n is β, and a projection angle of β on a vertical plane where the rotation axis p of the gantry is positioned is β', and β' satisfies following conditions: 0°<β'≤90°. Since the included angle between the central beam axis of the first imaging beam 220 and the reference line n is adjustable, the position between the entire treatment component 100 and the first imaging component 200 can be adjusted, thereby adapting to different mounting requirements.

In an embodiment, when it is necessary to mount the CT imaging component (such as the electronic computed tomography imaging component) on the radiation therapy system, since the entire CT imaging component has many components and large sizes, the larger mounting space is required. The CT imaging component must also be strictly guaranteed to be mounted in the same radial plane as the treatment component 100 on the gantry. In this case, the included angle β between the central beam axis of the first imaging beam 220 and the reference line n is set to a large value, so that β' is 70° or 80°, etc. As a result, the distance between the second radiation source 210 and the first radiation source 110 in the direction of the rotating axis p of the gantry can be longer, thereby effectively ensuring the mounting space of the entire CT imaging component.

In another embodiment, when the radiation therapy system does not need to be mounted on the CT imaging component, the included angle between the central beam axis of the first imaging beam 220 and the reference line n can be set to a larger value, so that β' is 10° or 20°, etc., so that the size of the entire radiation therapy system in the extending direction of the rotation axis p is relatively small and the structure is more compact. Specifically, when the second radiation source 210 is rotated around the axis in the xx' direction in FIG. 14 or FIG. 15, for example, as shown in FIG. 16 and FIG. 17, the relative position between the second radiation source 210 and the first radiation source 110 can be changed, so that the projection angle β' of the included angle β between the central beam axis of the first imaging beam 220 and the reference line n on the vertical plane where the rotation axis p of the gantry is positioned changes.

It should be noted that a specific value of the included angle β can be selected during the manufacturing process of the radiation therapy system, and when the manufacturing process is completed, the included angle β will no longer change, so that the projection angle β' of the included angle β on the vertical plane where the rotation axis p of the gantry is positioned will no longer change. It is also possible to configure different mounting positions on the gantry, so that the second radiation source 210 is mounted at different mounting positions, thereby changing the angle of the included angle β, which is not limited thereto.

Referring to FIG. 3, in the radiation therapy system provided by some embodiments of the present disclosure, the vertical line passing through the isocenter of the radiation therapy system is taken as the reference line n. The reference line n is perpendicular to the x-x'-y-y' plane. The included angle between the central beam axis of the first imaging beam 220 and the reference line n is β, a projection angle of β on the rotation plane of the first radiation source 110 is β", and β" satisfies following conditions: 0°≤β"≤90°. By changing the projection angle β" of β on the rotation plane of the first radiation source 110, the positions of the second radiation source 210 and the first radiation source 110 can be changed, thereby adapting to different mounting requirements.

Specifically, in order to avoid interference between the first radiation source 110 and the second radiation source 210, the angle of the projection angle β" of β on the rotation plane of the first radiation source 110 can be adjusted, so that the treatment beam 120 emitted by the first radiation source 110 does not irradiate the second radiation source 210, thereby avoiding damage to the second radiation source 210.

In an embodiment, when it is necessary to further mount the CT imaging component (such as the electronic computed tomography imaging component) on the radiation therapy system, in order to avoid interference between the radiation source and a detector in the CT imaging component and the second radiation source 210, the angle of the projection angle β" of β on the rotation plane of the first radiation source 110 can be adjusted.

It should be noted that the specific value of the included angle β can be selected during the manufacturing process of the radiation therapy system, and when the manufacturing process is completed, the included angle β will no longer change, so that the projection angle β" of β on the rotation plane of the first radiation source 110 will no longer change. It is also possible to configure different mounting positions on the gantry, so that the second radiation source 210 is mounted at different mounting positions, thereby changing the angle of the included angle β", which is not limited thereto.

It should be noted that the above angles θ and β can be flexibly changed individually or in combination according to the physical space requirements and imaging requirements of the mounting, thereby changing the values of θ', β' and β" to adapt different mounting requirements.

In some embodiments, the first radiation source 110 and the second radiation source 210 are relatively fixed on the gantry. After the first radiation source 110 and the second radiation source 210 are mounted and fixed relative to the gantry, the first radiation source 110 and the second radiation source 210 are not easy to shake relative to the gantry, which further strengthens the stability of the entire radiation therapy system, thereby improving an accuracy of the treatment.

Referring to FIG. 1, FIG. 3, FIG. 5, FIG. 8, FIG. 9, FIG. 12, FIG. 14 and FIG. 15, the treatment component 100 of the radiation therapy system according to some embodiments of the present disclosure further includes a first detector 130 arranged opposite to the first radiation source 110, and the first detector 130 is configured to receive at least part of the treatment beam 120. The first imaging component 200 further includes a second detector 230 arranged opposite to the second radiation source 210, and the second detector 230 is configured to receive at least part of the first imaging beam 220.

When the first radiation source 110 emits the treatment beam 120 and the treatment beam 120 passes through the treatment area of the target object 400, the first detector 130 can receive the treatment beam 120 passing through the target object 400, and transmit information on a dose of the treatment beam 120, so as to estimate a therapeutic dose received by the target object 400 by the information. When the second radiation source 210 emits an imaging beam and the imaging beam passes through the imaging area of the target object 400, the second detector 230 can receive the first imaging beam 220 passing through the target object 400, and convert the first imaging beam 220 into an image signal for transmission.

In some embodiments, the first radiation source 110 may also emit a third imaging beam capable of imaging the treatment area of the target object 400.

In some embodiments, the first radiation source 110 can be switched to emit the treatment beam 120 or the third imaging beam according to actual needs. For example, the first radiation source 110 may emit a beam with energy of 6 MV, which can be used for both therapy and imaging.

In some other embodiments, the first radiation source 110 can also be switched to emit beams with different energies according to actual needs, so as to form the treatment beam 120 or the third imaging beam. For example, the first radiation source 110 may emit a beam with energy of 6 MV as the treatment beam 120, which can be used for therapy, and the first radiation source 110 may emit a beam with energy of 1.5 MV as the third imaging beam, which can be used for imaging.

It should be noted that the energies of the first radiation source 110 and the second radiation source 210 of the radiation therapy system can be selected and adjusted according to actual needs, which is not limited thereto.

When the first radiation source 110 emits the third imaging beam and the third imaging beam passes through the treatment area of the target object 400, the first detector 130 can receive the third imaging beam passing through the target object 400 and transmit image information of the third imaging beam.

Referring to FIG. 12, in some embodiments, a side of the first detector 130 facing the first radiation source 110 is arcuate. Since the side of the first detector 130 facing the first radiation source 110 is arcuate, the length or width of the first detector 130 is smaller than that of a face-plate of a straight structure receiving the same treatment beam 120 or the third imaging beam, so that the structure of the entire radiation therapy system is more compact. Meanwhile, an edge beam of the treatment beam 120 or the third imaging beam can also be perpendicular to an arcuate receiving surface of the first detector 130, so that the imaging quality of the treatment component 100 is better.

Referring to FIG. 12, in some embodiments, a side of the second detector 230 facing the second radiation source 210 is arcuate. Since the side of the second detector 230 facing the second radiation source 210 is arcuate, the length or width of the second detector 230 is smaller than that of a face-plate of a straight structure receiving the same first imaging beam 220, further reducing the axial dimension of the entire radiation therapy system. Meanwhile, an edge beam of the first imaging beam 220 can also be perpendicular to an arc receiving surface of the second detector 230, so that the imaging quality of the first imaging component 200 is better.

It should be noted that either or both of the side of the first detector 130 facing the first radiation source 110 and the side of the second detector 230 facing the second radiation source 210 may be configured to be arcuate, which is not particularly limited thereto.

It should be noted that, when the side of the first detector 130 facing the first radiation source 110 is arcuate, a side facing away from the first radiation source 110 may be in any other shape, for example, it may be in an arcuate structure in FIG. 12, or it may also be in a planar structure, which is not particularly limited thereto.

It should be noted that, when the side of the second detector 230 facing the second radiation source 210 is arcuate, a side facing away from the second radiation source 210 may also be in any other shape, for example, it may be in an arcuate structure in FIG. 12, or it may also be in a planar structure, which is not particularly limited thereto.

Referring to FIG. 10, FIG. 11 and FIG. 13, in some embodiments, the radiation therapy system further includes a third detector 500 configured to receive at least part of the treatment beam 120 or the third imaging beam and at least part of the first imaging beam 220. The treatment beam 120 or the third imaging beam and the first imaging beam 220 are received by the third detector 500, so that the structure of the whole device is more compact and the mounting is more convenient. It should be noted that, a side of the third detector 500 facing the first radiation source 110 or the second radiation source 210 may be in a planar-face structure as shown in FIG. 10 and FIG. 11, or may be in an arcuate structure as shown in FIG. 13.

It should be noted that, when the side of the third detector 500 facing the first radiation source 110 or the second radiation source 210 is in the planar-face structure, the surface of the straight structure may be a planar surface, or may be a stepped surface formed by connecting multiple planar planes at an angle or parallel to each other. For example, the first detector 130 in FIG. 5 may be connected to the second detectors 230 on both sides respectively to form an overall stepped surface.

It should be noted that when the treatment beam 120 and the first imaging beam 220 are simultaneously received by the third detector 500, an irradiation area of the treatment beam 120 or the third imaging beam on the third detector 500 may overlap or may not overlap an irradiation area the first imaging beam 220 on the third detector 500.

In an embodiment, the irradiation area of the treatment beam 120 or the third imaging beam and the irradiation area of the first imaging beam 220 on the third detector 500 overlap, so that the length or width of the third detector 500 is relatively small, and the structure of the whole radiation therapy system is also relatively compact.

In another embodiment, the irradiated areas of the treatment beam 120 and the first imaging beam 220 on the third detector 500 do not overlap, which is beneficial to the analytical analysis of the treatment beam 120 and the first imaging beam 220.

It should be noted that when the treatment beam 120 and the first imaging beam 220 are simultaneously received by the third detector 500, and when the radiation therapy system performs imaging during the treatment process, the first imaging beam 220 can be controlled to emit the beam in the gap between the emissions of the treatment beam 120 to avoid mutual interference between the two signals. The treatment beam 120 and the first imaging beam 220 can also be emitted at the same time, and the treatment beam 120 received by the third detector 500 can be removed by an algorithm, so as to obtain a real-time signal of the first imaging beam 220. Specifically, according to a treatment plan, a dose of the treatment beam 120 irradiating the third detector 500 after passing through a human body can be simulated and calculated by Monte Carlo simulation and Boltzmann equation, etc., and an ionization chamber of the first radiation source 110 can also measure an emission dose in real-time to ensure that the emission dose of the actual treatment beam 120 is accurate. When the third detector 500 receives the signals from the treatment beam 120 and the first imaging beam 220 at the same time, for the overlapping area, the signal of the treatment beam 120 calculated according to the aforementioned method can be subtracted from the total signals to obtain remaining signals from the first imaging beam 220.

It should be noted that when the treatment beam 120 and the first imaging beam 220 are simultaneously received by the third detector 500, a parameter about a tilt angle between the first imaging beam 220 and the third detector 500 is calibrated as an input of a back-projection algorithm to obtain spatial position information of imaging, thereby ensuring the precision and accuracy of the imaging. Specifically, by calibrating a parameter about a tilt angle parameter between a beam corresponding to each pixel on the third detector 500 and the third detector 500, and determining spatial information of each beam based on the parameter about the tilt angle, the spatial position information of the imaging is obtained to ensure the precision and accuracy of the imaging.

It should be noted that, since the detector of the treatment beam 120 and the detector of the first imaging beam 220 have different sensitivities, scintillators selected by them are also different. For example, the detector of the treatment beam 120 receives a beam of MV level, so a first material is selected for reception. Specifically, the first material may be gadolinium oxysulfide. The detector of the first imaging beam 220 receives a beam of KV level, so a second material is selected for reception. Specifically, the second material may be cesium iodide.

When the treatment beam 120 and the first imaging beam 220 are simultaneously received by the third detector 500, different scintillators may be set in different areas of the same layer of the third detector 500. For example, the first material (gadolinium oxysulfide) for receiving the beam of MV level is arranged in a middle area facing the treatment beam 120, and the second material (cesium iodide) for receiving the beam of KV level is arranged in two side areas facing the first imaging beam 220, so as to achieve simultaneous reception of the treatment beam 120 and the first imaging beam 220 by one detector. The third detector 500 can also be arranged in two layers, the layer on the side facing the radiation source is provided with the second material (cesium iodide) for receiving the beam of KV level, and the layer on the side away from the radiation source is provided with the first material (gadolinium oxysulfide) for receiving the beam of MV level, so that the treatment beam 120 and the first imaging beam 220 can be simultaneously received by the one detector.

Referring to FIGS. 1 to 4, in some embodiments, the number of the first imaging component 200 is one. When the first imaging component 200 is a digital radiography (DR) imaging component (for example, a digital X-ray imaging component), the radiation therapy system is a single DR radiation therapy system by providing one first imaging component 200. The digital X-ray imaging component may include an x-ray tube, a high-pressure generator, a beam limiting device, a digital image processing and a flat panel detector. When the first imaging component 200 is the digital X-ray imaging component, the second radiation source corresponds to the x-ray tube.

Referring to FIGS. 5 to 17, in some embodiments, the number of the first imaging component 200 is two, and the second radiation sources 210 of the two first imaging components 200 are spaced apart. Rotation planes of the two second radiation sources 210 of the first imaging component 200 may be distributed in a direction along the rotation axis and spaced from each other. By providing the two first imaging components 200, when the radiation therapy system treats the target object 400, two second radiation sources 210 can emit imaging beams and the imaging beams pass through the imaging area of the target object 400, so as to obtain information on the target object 400 from at least two angles, and determine a three-dimensional position of the target object 400. In a specific embodiment, the two first imaging components 200 are both DR imaging components (digital X-ray imaging components). By setting two DR imaging components, the radiation therapy system is a dual DR radiation therapy system.

In some embodiments, the two second radiation sources 210 of the first imaging component 200 are arranged symmetrically in the central beam axis of the first radiation source 110.

In still some embodiments, the two second radiation sources 210 are arranged symmetrically in the x-x'-y-y' plane, the x-x'-z-z' plane or the y-y'-z-z' plane passing through the isocenter of the radiation therapy system.

Referring to FIG. 14 and FIG. 15, the radiation therapy system according to an embodiment of the present disclosure further includes a second imaging component 600 mounted on the gantry. The second imaging component 600 and the first radiation source 110 are arranged on the same radial plane of the gantry. The second imaging component 600 includes a third radiation source 610 and a fourth detector 620 arranged opposite to the third radiation source 610. The third radiation source 610 is configured to emit a second imaging beam to the imaging area of the target object 400, and the fourth detector is configured to receive at least part of the second imaging beam. The fourth detector may be, for example, arcuate. Specifically, the second imaging component 600 is the CT imaging component, and the CT imaging component is mounted on the radial plane of the gantry where the treatment component 100 is positioned. The third radiation source 610 can emit the second imaging beam to the imaging area of the target object 400, and the fourth detector can receive at least part of the second imaging beam, and convert the second imaging beam into an image signal for transmission. The CT imaging component includes an electronic computed tomography imaging component. The electronic computed tomography imaging component may include an X-ray tube, a high-pressure generator and a detector. When the second imaging component 600 is the electronic computed tomography imaging component, the third radiation source 610 corresponds to the X-ray tube.

It should be noted that since the CT imaging component is mounted on the radial plane of the gantry where the treatment component 100 is positioned, a diagnostic-level CT imaging position overlaps a treatment position, avoiding additional errors caused by moving the patient due to the imaging position not overlapping the treatment position.

As shown in FIG. 14, the second imaging component 600 and the treatment component 100 may be arranged such that a central beam axis of the second imaging beam emitted by the third radiation source 610 is substantially perpendicular to the central beam axis of the treatment beam 120 emitted by the first radiation source 110. Alternatively, in other embodiments, the central beam axis of the second imaging beam emitted by the third radiation source 610 may not be perpendicular to the central beam axis of the treatment beam 120 emitted by the first radiation source 110, as long as the second imaging beam emitted by the third radiation source 610 is not blocked by the first radiation source 110 and the treatment beam 120 emitted by the first radiation source 110 is not blocked by the third radiation source 610.

As described above, the second imaging component 600 and the treatment component 100 are positioned in the same radial plane of the gantry, while the first imaging component 200 is positioned in a different radial plane of the gantry from both the second imaging component 600 and the treatment component 100. In some embodiments, all of the first radiation source 110, the second radiation source 210 and the third radiation source 610 are relatively fixed on the gantry. When the target object is treated by the radiation therapy system, the gantry can synchronously drive the first radiation source 110, the second radiation source 210 and the third radiation source 610 to rotate synchronously, so that the treatment beam 120 emitted by the first radiation source 110 is not be blocked by the second radiation source 210 or the third radiation source 610, the first imaging beam 220 emitted by the second radiation source 210 is not be blocked by the first radiation source 110 or the third radiation source 610, and the second imaging beam emitted by the third radiation source 610 is not be blocked by the first radiation source 110 or the second radiation source 610. As a result, no blind spot which cannot be imaged will be generated, and the imaging effect in the whole treatment process is better. Furthermore, the judgment of the user on the treatment situation is more accurate, and the misjudgment is not easy to occur.

In some embodiments, the second radiation source 210 is a radiation source of a digital X-ray imaging component, and the third radiation source 610 is a radiation source of the electronic computed tomography imaging component. Therefore, the first imaging component 200 is the digital X-ray imaging component, i.e., the above-mentioned DR imaging component. The second imaging component 600 is the electronic computed tomography imaging component, i.e., the above-mentioned CT imaging component.

When the radiation therapy system needs to integrate one treatment component 100, two DR imaging components and one CT imaging component, since it is necessary to ensure that the treatment component 100 and the CT imaging component are mounted on the same radial plane of the gantry, as shown in FIG. 14 or FIG. 15, the two DR imaging components are rotated in the x-x' axis, or the y-y' axis, or the z-z' axis, so as to change a mounting position of the DR imaging component to effectively ensure the mounting space of the entire CT imaging component. Meanwhile, on the premise of effectively ensuring the mounting space of the CT imaging component, the size of the entire radiation therapy system in the direction along the rotation axis p can be reduced, making the structure of the entire radiation therapy system more compact.

It should be noted that when the radiation therapy system includes one CT imaging component and two DR imaging components, in some embodiments, the two second radiation sources 210 can be respectively arranged on different sides of the third radiation source 610 in the direction along the rotation axis, such as shown in FIG. 16 and FIG. 17, which is beneficial to adjust the balance of the whole system, so that the structure of the whole system is more symmetrical and not easy to fall over. Certainly, in some other embodiments, the two second radiation sources 210 can also be arranged on the same side of the third radiation source 610 in the direction along the rotation axis, which is easy to mount.

The technical features in the above embodiments can be combined arbitrarily. For concise description, not all possible combinations of the technical features in the above embodiments are described. However, all the combinations of the technical features are to be considered as falling within the scope described in this specification provided that they do not conflict with each other.

The above-mentioned embodiments only describe several implementations of the present disclosure, and their description is specific and detailed, but should not be understood as a limitation on the patent scope of the present disclosure. It should be pointed out that for those skilled in the art may further make variations and improvements without departing from the conception of the present disclosure, and these all fall within the protection scope of the present disclosure. Therefore, the protection scope of the present disclosure should be subject to the appended claims.

What is claimed is:

1. A radiation therapy system, comprising:

a gantry having a rotation axis;

a first radiation source mounted on the gantry, the first radiation source being configured to emit a treatment beam to a treatment area of a target object; and at least one second radiation source mounted on the gantry, the at least one second radiation source being configured to emit an imaging beam to an imaging area of the target object, the imaging area at least partially overlapping the treatment area;

wherein the first radiation source and the at least one second radiation source are relatively fixed on the gantry, the first radiation source and the at least one second radiation source are rotatable around the rotation axis, and a rotation plane of the first radiation source and a rotation plane of the at least one second radiation source are distributed and spaced apart in a direction along the rotation axis so that the first radiation source and the second radiation source are positioned in different radial planes of the gantry along the rotation axis.

2. The radiation therapy system of claim 1, wherein at least one of the first radiation source and the at least one second radiation source is mounted on the gantry by an adjustable connecting mechanism configured to extend and move in at least one of an axial direction, a circumferential direction or a radial direction of the gantry, such that a position of the at least one of the first radiation source and the at least one second radiation source relative to the gantry is adjusted.

3. The radiation therapy system of claim 1, wherein a central beam axis of the imaging beam and the rotation axis of the gantry form an included angle of θ, the included angle forming a projection angle of θ' on a horizontal plane, the θ' satisfying following conditions:

$$0° \leq \theta' < 90°.$$

4. The radiation therapy system of claim 3, wherein the θ is 30°, 45° or 60°.

5. The radiation therapy system of claim 1, wherein when a vertical line passing through an isocenter of the radiation therapy system is set as a reference line, the central beam axis of the imaging beam and the reference line form an included angle of β, the included angle forming a projection angle of β' on a vertical plane where the rotation axis of the gantry is positioned, the β' satisfying following conditions:

$$0° < \beta' \leq 90°.$$

6. The radiation therapy system of claim 1, wherein when a vertical line passing through an isocenter of the radiation therapy system is set as a reference line, the central beam axis of the imaging beam and the reference line form an included angle of β, the included angle forming a projection angle of β" on the rotation plane of the first radiation source, the β" satisfying following conditions:

$$0° \leq \beta'' \leq 90°.$$

7. The radiation therapy system of claim 1, wherein the gantry is configured to drive the first radiation source and the at least one second radiation source such that the first radiation source and the at least one second radiation source rotate synchronously.

8. The radiation therapy system of claim 1, wherein the radiation therapy system further comprises a first detector arranged opposite to the first radiation source, the first detector being mounted on the gantry and configured to receive at least part of the treatment beam.

9. The radiation therapy system of claim 8, wherein a side of the first detector facing the first radiation source is arcuate.

10. The radiation therapy system of claim 1, wherein the radiation therapy system further comprises a second detector arranged opposite to a corresponding one of the at least one second radiation source, the second detector being mounted on the gantry and configured to receive at least part of the imaging beam.

11. The radiation therapy system of claim 10, wherein a side of the second detector facing the corresponding second radiation source is arcuate.

12. The radiation therapy system of claim 1, wherein the radiation therapy system further comprises a third detector configured to receive at least part of the treatment beam and at least part of the imaging beam.

13. The radiation therapy system of claim 1, wherein the number of the at least one second radiation source is two, and the two second radiation sources are spaced apart.

14. The radiation therapy system of claim 1, wherein the radiation therapy system comprises a first imaging component including the at least one second radiation source, and the radiation therapy system further comprises:

a second imaging component mounted on the gantry, the second imaging component and the first radiation source being arranged in a same radial plane of the gantry.

15. The radiation therapy system of claim 14, wherein the second imaging component comprises a third radiation source and a fourth detector arranged opposite to the third radiation source, the third radiation source being configured to emit a further imaging beam to the imaging area of the target object, and the fourth arcuate detector being configured to receive at least part of the further imaging beam.

16. The radiation therapy system of claim 15, wherein when the number of the at least one second radiation source is two, the two second radiation sources are arranged on a same side of the third radiation source in the direction along the rotation axis.

17. The radiation therapy system of claim 15, wherein when the number of the at least one second radiation source is two, the two second radiation sources are respectively arranged on different sides of the third radiation source in the direction along the rotation axis.

18. The radiation therapy system of claim 14, wherein the first imaging component is a digital X-ray imaging component.

19. The radiation therapy system of claim 14, wherein the second imaging component is an electronic computed tomography imaging component.

* * * * *